(12) United States Patent
Hlavka

(10) Patent No.: US 11,944,654 B2
(45) Date of Patent: *Apr. 2, 2024

(54) BACTERIOTHERAPY FOR CLOSTRIDIUM DIFFICILE COLITIS

(71) Applicant: Rebiotix, Inc., Roseville, MN (US)

(72) Inventor: Edwin J. Hlavka, Minneapolis, MN (US)

(73) Assignee: Rebiotix, Inc., Roseville, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/886,274

(22) Filed: Aug. 11, 2022

(65) Prior Publication Data

US 2023/0076826 A1 Mar. 9, 2023

Related U.S. Application Data

(63) Continuation of application No. 15/964,228, filed on Apr. 27, 2018, now Pat. No. 11,446,337, which is a continuation of application No. 15/251,725, filed on Aug. 30, 2016, now abandoned, which is a continuation of application No. 14/093,913, filed on Dec. 2, 2013, now Pat. No. 9,463,208, which is a continuation of application No. 13/576,573, filed as application No. PCT/US2011/000184 on Feb. 1, 2011, now Pat. No. 9,629,881.

(60) Provisional application No. 61/351,184, filed on Jun. 3, 2010, provisional application No. 61/337,283, filed on Feb. 1, 2010.

(51) Int. Cl.
| | |
|---|---|
| *A61K 35/741* | (2015.01) |
| *A61K 9/20* | (2006.01) |
| *A61K 35/74* | (2015.01) |
| *C12N 1/04* | (2006.01) |
| *C12N 1/20* | (2006.01) |
| *G01N 33/569* | (2006.01) |

(52) U.S. Cl.
CPC .............. *A61K 35/741* (2013.01); *A61K 9/20* (2013.01); *A61K 35/74* (2013.01); *C12N 1/04* (2013.01); *C12N 1/20* (2013.01); *G01N 33/56911* (2013.01); *G01N 2333/33* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 3,261,761 A | 7/1966 | Anderson | |
| 5,364,756 A | 11/1994 | Livesey et al. | |
| 5,443,826 A | 8/1995 | Borody | |
| 5,837,238 A | 11/1998 | Casas et al. | |
| 5,902,578 A | 5/1999 | Halpin-Dohnalek et al. | |
| 6,391,224 B1 | 5/2002 | Wowk | |
| 6,428,783 B1 | 8/2002 | Khachatrian et al. | |
| 6,635,260 B1 | 10/2003 | Gerding | |
| 6,645,530 B1 | 11/2003 | Borody | |
| 7,307,062 B2 | 12/2007 | Bolte | |
| 8,460,648 B2 | 6/2013 | Borody | |
| 8,722,088 B2 | 5/2014 | Olesen et al. | |
| 9,011,834 B1 | 4/2015 | McKenzie et al. | |
| 9,433,651 B2 | 9/2016 | Jones et al. | |
| 9,463,208 B2 | 10/2016 | Hlavka | |
| 9,511,100 B2 | 12/2016 | Jones et al. | |
| 9,629,881 B2 | 4/2017 | Hlavka | |
| 9,642,880 B2 | 5/2017 | Jones et al. | |
| 9,675,648 B2 | 6/2017 | Jones et al. | |
| 9,694,039 B2 | 7/2017 | Jones et al. | |
| 9,782,445 B2 | 10/2017 | Jones et al. | |
| 10,226,431 B2 | 3/2019 | Jones et al. | |
| 10,383,901 B2 | 8/2019 | Jones et al. | |
| 10,391,064 B2 | 8/2019 | Jones et al. | |
| 10,391,129 B2 | 8/2019 | Jones et al. | |
| 10,434,124 B2 | 10/2019 | Jones et al. | |
| 10,434,125 B2 | 10/2019 | Jones et al. | |
| 10,434,126 B2 | 10/2019 | Jones et al. | |
| 10,471,107 B2 | 11/2019 | Jones et al. | |
| 10,493,111 B2 | 12/2019 | Jones et al. | |
| 10,603,341 B2 | 3/2020 | Jones et al. | |
| 10,610,547 B2 | 4/2020 | Jones et al. | |
| 10,624,932 B2 | 4/2020 | Jones et al. | |
| 10,688,137 B2 | 6/2020 | Jones et al. | |

(Continued)

FOREIGN PATENT DOCUMENTS

| | | |
|---|---|---|
| CN | 107921072 A | 4/2018 |
| CN | 107949391 A1 | 4/2018 |

(Continued)

OTHER PUBLICATIONS

Borody, Thomas J; et al; "Bacteriotherapy Using Fecal Flora: Toying With Human Motions" Journal of Clinical Gastroenterology,. 38, 475-483, 2004 (Year: 2004).*

Aas et al., "Recurrent Clostridium difficile Colitis: Case Series Involving 18 Patients Treated with Donor Stool Administered via a Nasogastric Tube," Clin Infect Dis, vol. 36, (Mar. 2003), pp. 580-585.

(Continued)

*Primary Examiner* — David W Berke-Schlessel

(74) *Attorney, Agent, or Firm* — Foley & Lardner LLP

(57) ABSTRACT

This document discusses, among other things, receiving a plurality of donor fecal samples from a plurality of donors and storing and indexing each respective donor fecal samples using at least one characteristic of the respective donor fecal sample. In an example, the donor fecal sample can be screened and processed for subsequent use in fecal bacteriotherapy to displace pathogenic or undesired organisms in the digestive track of a patient with healthy or desirable gut microbiota.

11 Claims, 3 Drawing Sheets

(56) References Cited

U.S. PATENT DOCUMENTS

| | | |
|---|---|---|
| 10,799,539 B2 | 10/2020 | Jones et al. |
| 10,828,340 B2 | 11/2020 | Jones et al. |
| 10,905,726 B2 | 2/2021 | Jones et al. |
| 11,446,337 B2 | 9/2022 | Hlavka |
| 11,554,143 B2 | 1/2023 | Jones et al. |
| 2002/0022019 A1 | 2/2002 | Laulund |
| 2003/0031659 A1 | 2/2003 | Farmer |
| 2004/0062757 A1 | 4/2004 | Finegold |
| 2004/0167062 A1 | 8/2004 | Bolte |
| 2004/0170617 A1 | 9/2004 | Finegold |
| 2005/0074441 A1 | 4/2005 | Collins et al. |
| 2006/0008511 A1 | 1/2006 | Lin et al. |
| 2007/0212674 A1 | 9/2007 | Spiers |
| 2008/0089870 A1 | 4/2008 | Ghosh et al. |
| 2008/0208158 A1 | 8/2008 | Goodman et al. |
| 2008/0254009 A1 | 10/2008 | Finegold |
| 2009/0138354 A1 | 5/2009 | Zech |
| 2010/0242124 A1 | 9/2010 | Glimcher et al. |
| 2010/0316617 A1 | 12/2010 | Renaud et al. |
| 2011/0129529 A1 | 6/2011 | Lin |
| 2012/0252775 A1 | 10/2012 | Finegold |
| 2012/0276059 A1 | 11/2012 | Boone et al. |
| 2012/0276060 A1 | 11/2012 | Boone et al. |
| 2013/0022575 A1 | 1/2013 | Cassity |
| 2013/0045274 A1 | 2/2013 | Hlavka |
| 2013/0052172 A1 | 2/2013 | Baker |
| 2013/0064885 A1 | 3/2013 | Lin et al. |
| 2013/0108598 A1 | 5/2013 | Oresic et al. |
| 2013/0149339 A1 | 6/2013 | Honda et al. |
| 2013/0195804 A1 | 8/2013 | Borody |
| 2013/0195820 A1 | 8/2013 | Wacklin et al. |
| 2013/0266539 A1 | 10/2013 | Borody |
| 2014/0174692 A1 | 6/2014 | Emond et al. |
| 2014/0363400 A1 | 12/2014 | Jones et al. |
| 2015/0093360 A1 | 4/2015 | McKenzie et al. |
| 2016/0113974 A1 | 4/2016 | Jones et al. |
| 2016/0201053 A1 | 7/2016 | Maizels et al. |
| 2016/0250151 A1 | 9/2016 | Bochenek et al. |
| 2016/0339065 A1 | 11/2016 | Adams et al. |
| 2016/0367607 A1 | 12/2016 | Hlavka |
| 2017/0100688 A1 | 4/2017 | Davidson et al. |
| 2017/0266241 A1 | 9/2017 | Hlavka |
| 2018/0000872 A1 | 1/2018 | Hamilton et al. |
| 2018/0078586 A1 | 3/2018 | Jones et al. |
| 2019/0365831 A1 | 12/2019 | Jones et al. |
| 2020/0230182 A1 | 7/2020 | Jones et al. |
| 2021/0137999 A1 | 5/2021 | Jones et al. |
| 2021/0138000 A1 | 5/2021 | Jones et al. |
| 2023/0310516 A1 | 10/2023 | Jones et al. |
| 2023/0364159 A1 | 11/2023 | Jones et al. |

FOREIGN PATENT DOCUMENTS

| | | |
|---|---|---|
| EP | 1 300 472 A1 | 4/2003 |
| EP | 1 340 078 B1 | 9/2003 |
| EP | 1 432 786 B1 | 6/2004 |
| EP | 2 636 684 A1 | 9/2013 |
| EP | 2 783 688 A1 | 10/2014 |
| WO | WO-89/05659 A1 | 6/1989 |
| WO | WO-01/93904 A1 | 12/2001 |
| WO | WO-02/07741 A1 | 1/2002 |
| WO | WO-2011/094027 A1 | 8/2011 |
| WO | WO-2012/013861 A2 | 2/2012 |
| WO | WO-2012/016287 A2 | 2/2012 |
| WO | WO-2012/024638 A2 | 2/2012 |
| WO | WO-2012/033814 A3 | 3/2012 |
| WO | WO-2012/122478 A1 | 9/2012 |
| WO | WO-2012/122522 A1 | 9/2012 |
| WO | WO-2012/142605 A1 | 10/2012 |
| WO | WO-2012/149351 A1 | 11/2012 |
| WO | WO-2013/053836 A1 | 4/2013 |
| WO | WO-2013/090825 A1 | 6/2013 |
| WO | WO-2013/130773 A2 | 9/2013 |
| WO | WO-2013/163582 A1 | 10/2013 |
| WO | WO-2013/171515 A1 | 11/2013 |
| WO | WO-2014/152484 A1 | 9/2014 |
| WO | WO-2016/196605 A1 | 12/2016 |
| WO | WO-2016/201114 A1 | 12/2016 |
| WO | WO-2017/118924 A1 | 7/2017 |

OTHER PUBLICATIONS

Aas, J et al, C Diff Treatment with Fecal Transplant, Stool transplantation for older patients with clostridium difficile infection, 2009.

Abbeele et al., "Microbial Community Development in a Dynamic Gut Model Is Reproducible, Colon Region Specific, and Selective for Bacteroidetes and Clostridium Cluster IX," Applied and Environmental Microbiology, vol. 76, No. 15, pp. 5237-5246 (Aug. 2010).

Abubaker, I et al, Microbiome papers, Health Technology Assesmenl 2007 vol. 11 No. 36, 2007.

Acha, S.J. et al, Microbe preservation, Changes of viability and composition of the Escherichia coli flora in faecal samples during long term storage, 2005.

Adams, Stephen, et al, Ulcerative Colitis, Ulcerative Colitis, 2013.

Adler, A., et al., "Trends and Changes in Clostridium difficile Diagnostic Profiles and Their Impact on the Proportion of Positive Samples: a National Survey", Clin. Microbiol Infect. Mar. 27, 2014, 10.1111/1469-0691.12634.

Agar Plate Info, BBL Bacteroides Bile Esculin Agar {BBE), 2006.

Ali, Shanom, Healthcare industry, Diverse sources of C. difficile infection, 2014.

Allen, Stephen et al, Drug Delivery, Lactobacilli and bifidobacteria in the prevention of antibiotic- associated diarrhea and clostridium difficile diarrhea in older inpatients {PLACIDE): a randomized, double-blind, placebo-controlled, multicentre trial, 2013.

Allen-Vercoe, Emma et al, C Diff Treatment with Fecal Transplant, A canadian working group report on fecal microbial therapy: microbial ecosystems therapeutics, 2012.

Alonso, Carolyn; Marr, Kieren, C Diff Studies, Colostridium difficile infection among hematopoietic stem cell transplant recipients: beyond colitis, 2013.

Alsharif, R., et al., Counting Bacteria, Bacterial detection and live/dead discrimination by flow cytometry, 2002.

Amann, RI et al, Counting Bacteria, Combination of 16S rRNA-targeted oligonucleotide probes with flow cytometry for analyzing mixed microbial populations, 1990.

Ananthakrishnan, A. et al, GI Disease—General, Genetic risk factors for Colostridium difficile infection in ulcerative colitis, 2013.

Andoh, A. et al, Chrohn's Disease, Multicenter analysis of fecal microbiota profiles in Japanese patients with Chron's disease, 2012.

Angelberger, S. et al, Ulcerative Colitis, Temporal bacterial community dynamics vary among uncerative colitis patients after fecal microbiota transplantation, 2013.

Ariefdjohan et al., "Comparison of DNA extraction kits for PCR-DGGE analysis of human intestinal microbial communities from fecal specimens," Nutrition Journal, vol. 9 No. 23, pp. 1-8 (May 2010).

Arkkila, P. E., C Diff Treatment with Fecal Transplant, Fecal bacteriotherapy for recurrent clostridium difficile infection, 2011.

Aronoff, D.M., "Host-Pathogen Interactions in Clostridium difficile Infection: It Takes Two to Tango", Clin Infect Dis. (2014) 58 (10):1401-1403.

Arthur, J.; Jobin, C., Cancer, The struggle within: microbial influences on colorectal cancer, 2011.

Arumugam, M. et al, Analysis of Species in Feces, Enterotypes of the human gut microbiome, 2011.

Arvand, M., et al., "Increased incidence of Clostridium difficile PCR ribotype 027 in Hesse, Germany, 2011 to 2013", Euro Surveill, 2014:19(10) 1-6.

Aslam, S. et al, C Diff Studies, Treatment of clostridium difficile-associated disease: old therapies and new strategies, 2005.

Aspevall, 0., et al., "Performance of Four Chromogenic Urine Culture Media after One or Two Days of Incubation Compared with Reference Media", Journal of Clinical Microbiology, vol. 40, No. 4, Apr. 2002, 1500-1503.

(56) References Cited

OTHER PUBLICATIONS

ASTM International, "Standard Practice for Climatic Stressing of Packaging Systems for Single Parcel Delivery", Book of Standards vol. 15.10, 2010, 10.1520/F2825-10E01 (3 pgs.).

Atarashi, K. et al, Analysis of Species in Feces, Treg introduction by a rationally selected mixture of colostrudia strains from the human microbiota, 2013.

Austin, M., et al., "Fecal Microbiota Transplantation in the Treatment of Clostridium difficile Infections", The American Journal of Medicine (2014), doi: 10.1016/j.amjmed.2014.02.017 (15 pgs.).

Aye et al., "Assessment of the Genotoxicity of three cryoprotectants used for human oocyte vitrification: Dimethyl sulfoxide, ethylene glycol and propylene glycol," Food and Chemical Toxicology, vol. 48, pp. 1905-1912 (2010).

Azad, M. et al., Pediatrics, Gut microbiota of healthy canadian infants: profiles by mode of delivery and infant diet at 4 months, 2013.

Backhed, Fredrik et al, Gut Microbiome News, Host-Bacterial mutualism in the human intestine, 2005.

Baheti et al., "Excipients used in lyophilization of small molecules," J. Excipients and Food Chem. vol. 1 No. 1, (2010).

Bahl, et al, Microbe preservation, Freezing fecal samples prior to DNA extraction affects the Finrnicutes toBacteroidetes ratio determined by downstream quantitative PCR analysis, 2011.

Bakken, J., et al., "Treating Clostridium difficile Infection With Fecal Microbiota Transplantation", Clinical Gastroenterology and Hepatology 2011;9: 1044-1049.

Bakken, J.S., "Fecal baceriotherapy for recurrent Clostridium difficile infection", Anaerobe 15 (2009) 285-289.

Bakken, Johan et al, C Diff Studies, Treatment approaches including fecal microbiota transplantation for recurrent Clostridium difficile infection {RCDI} among infectious disease physicians, 2013.

Bakken, Johan et al, C Diff Treatment with Fecal Transplant, Treating clostridium difficile infection with fecalmicrobiota transplantation, 2011.

Barbut, F., et al., "Does a rapid diagnosis of Clostridium difficile infection impact on quality of patient management?", Clinical Microbiology and Infection, vol. 20, No. 2, Feb. 2014, 136-144.

Barletta, J. et al, Intestinal pH, Proton pump inhibitors and the risk for hospital aquired colostridium difficile infection, 2013.

Baron, Todd, C Diff Treatment with Fecal Transplant, Fecal Microbiota Transplant: We know its history, but can we predict its future?, 2013.

Barr, David, Industry, CGMPs in the production of clinical supplies, 2007.

Bartlett, J., "A Call to Arms: The Imperative for Antimicrobial Stewardship", CID, 2011 :53 (Suppl 1) S4-S7.

Bauer, et al, C Diff Studies, Patients with cystic fibrosis have a high carriage rate of non-toxigenic Clostridium difficile 2013.

BD, Agar Plate Info, Brucella Blood Agar with Hemin and Vitamin K1, 2011.

Bell, Caitlin H, Centrifugation, The Effects of Centrifugation and Filtration as Pre-Treatments in Bacterial Retention Studies, 2005.

Ben-Amor, Kaouther et al, Analysis of Species in Feces, Genetic diversity of viable, injured and dead fecal bacteria assessed by fluorecence-activated cell sorting and 16S rRNA gene analysis, 2005.

Ben-Amor, Kaouther et al, Counting Bacteria, Multiparametric flow cytometry and cell sorting for the assessment of viable, injured, and dead bifidobacterium cells during bile salt stress, 2002.

Benjamin, et al, Chrohn's Disease, Smokers with Active Crohn's Disease Have a Clinically Relevant Dysbiosis of the Gastrointestinal Microbiota, 2011.

Bennet, Justin et al, C Diff Treatment with Fecal Transplant, Treatment of ulcerative colitis by implantation of normal colonic flora, 1989.

Bennett, P.S., et al., What Nurses Need to Know About Fecal Microbiota Transplantation: Education, Assessment, and Care for Children and Young Adults, J_ Pediatr Nurs., Feb. 7, 2014, doi: 10.1016/j.pedn.2014.01 .013 (8 pgs).

Berejnov, V. et al, Cryopreservation Studies, Effects of cryoprotectant concentration and cooling rate on vitrification of aqueous solutions, 2006.

Bervoets, L. et al, Pediatrics/Obesity Related, Differences in gut microbiota composition between obese and lean children: a cross-sectional study, 2013.

Best, E. et al, Industry, The Potential for Airborne Dispersal of Clostridium difficile from Symptomatic Patients, 2012.

Bhat, A. et al, Cryopreservation Studies, Bacillus subtilis natto: a non-toxic source of poly-y-glutamic acid that could be used as a cryoprotectant for probiotic bacteria, 2013.

Bodger, K. et al, Industry, Development and validation of a rapid, generic measure of disease control from the patient's perspective: the IBD-Control questionnaire, 2013.

Boenning, D.A., et al., "Clostridium difficile in a pediatric outpatient population", Pediatric Infectious Disease, vol. 1, No. 5, 336-338.

Bonavia et al., "Bacteria Cryopreservation Protocol: Protocol Exchange," 5 pages (2012) Available online, URL: http://www.nature.com/protocolexchange/protocols/2326.

Bonfrate, Leoni Ide et al, GI Disease—General, Microbiota in health and irritable bowel syndrome: currentknowledge, perspectives and therapeutic options, 2013.

Boone, J.H., et al., "Clostridium difficile prevalence rates in a large healthcare system stratified according to patient population, age, gender, and specimen consistency", Eur J Clin Microbiol Infect Dis (2012) 31:1551-1559.

Borody et al., "Bacteriotherapy Using Fecal Flora: Toying with Human Motions" J. Clin. Gastroenterol., vol. 38 No. 6, pp. 475-483 (Jul. 2004).

Borody et al., "Faecal bacteriotherapy (FB) for chronic C. difficile (Cd) syndromes," Journal of Gastroenterology and Hepatology 18 (Suppl.) (2003).

Borody, T J et al, Bowel disease treatment with FT, Bowel-flora alteration: a potential cure for inflammatory bowel disease and irritable bowel syndrome?, 1989.

Borody, T J et al, Bowel disease treatment with FT, Treatment of ulcerative colitis using fecal bacteriotherapy, 2003.

Borody, T J et al, C Diff Treatment with Fecal Transplant, Bacteriotherapy using fecal flora, 2004.

Borody, T J et al, C Diff Treatment with Fecal Transplant, Fecal microbiota transplantation: Indications, methods, evidence, and future directions, 2013.

Borody, T J et al, FMT Studies and Reviews, Therapeutic faecal microbiota transplantation: current status and future developments, 2014.

Bowden, Talmadge et al, Bowel disease treatment with FT, Pseudomembranous enterocolitis: mechanism of restoring floral homeostasis, 1981.

Brace, C., et al., "Microbial composition analysis of Clostridium difficile infections in an ulcerative colitis patient treated with multiple fecal microbiota transplantations", J Crohns Colitis (2014), http://dx.doi.org/10.1016/j.crohns.2014.01 .020 (5 pgs.).

Brahe, L.K. and Larson, L.H., Obesity Related, Is butyrate the link between diet, intestinal microbiota and obesity related metabolic diseases?, 2013.

Brandt, Lawrence, C-Diff Treatment with Fecal Transplant, Norovirus Gastroenteritis After Fecal Microbiota Transplantation for Treatment of Colostridium Difficile Infection Despite Asymptonatic Donors and Lack of Sick Contacts, 2013.

Brandt, Lawrence; Aroniadis, Olga, C Diff Treatment with Fecal Transplant, An overview of fecal microbiotatransplantation: techniques, indications and outcomes, 2013.

Brandt, Let al, C Diff Treatment with Fecal Transplant, American journal of gastroenterology lecture: intestinal microbiota and the role of fecal microbiota transplant (FMT) in treatment of c diff infection, 2012.

Brandt, Let al, C Diff Treatment with Fecal Transplant, Long-term follow-up of colonoscopic fecal microbiota transplant for recurrent clostridium difficile infection (paper and question/answer with Brandt), 2012.

(56) References Cited

OTHER PUBLICATIONS

Brecher, S. et al, C Diff Studies, Laboratory diagnosis of colostridium difficile infections: a practical guide for clinicians: there is a light at the end of the colon, 2013.
Britton, R., et al., Role of the Intestinal Microbiota in Resistance to Colonization by Clostridium difficle, Gastroenterology (2014) (19 pgs.).
Brown, J. et al, Microbiome papers, Translating the human microbiome, 2013.
Buffie, C.; Palmer, E., Microbiome papers, Microbiota-mediated colonization resistance against intestinal pathogens, 2013.
Burke, Kristin et al, C Diff Treatment with Fecal Transplant, Fecal Transplantation for recurrent colostridium difficile infection in older adults: a review, 2013.
Burnham, Carey-Ann; Carroll, Karen, C Diff studies, Diagnosis of colostridium difficile infection: an ongoing conundrum for clinicians and clinical laboratories, 2013.
C. Guerin-Danan, "Storage of intestinal bacteria in samples frozen with glycerol," Microbial Ecology in Health and Disease, vol. 11, No. 3, Jan. 1, 1999, pp. 180-182.
Calabrese, R. et al, Industry, Finding common ground with ISO 9001 and FDA Good Manufacturing Practices, 2013.
Cammarota, G. et al, FMT Studies and Reviews, Fecal Microbiota Transplantation for the Treatment of Clostridium difficile Infection A Systematic Review, 2014.
Cammarota, G. et al, FMT Studies and Reviews, Fecal transplantation for Colostridium difficile infection. Three cases treated in italy, 1993.
Cammarota, G., et al., "Gut microbiota modulation: probiotics, antibiotics or fecal microbiota transplantation?" Intern Emerg Med (2014), DOI: 10.1007/s11739-014-069-4 (9 pgs.).
Cardona, S. et al, Microbe preservation, Storage conditions of intestinal microbiota matter in metagenomic analysis, 2012.
Carroll, I et al, Analysis of Species in Feces, Characterization of the fecal microbiota using high-throughput sequencing reveals a stable microbial community during storage, 2012.
CDC, "Vital Signs: Preventing Clostridium difficile Infections", MMWR, Mar. 9, 2012, vol. 61, No. 9, 157-162.
CDC, Industry, Antibiotic resistance threats in the United States, 2013, 2013.
Chandel, N; Budlinger, G.R., Industry, The good and bad of antibiotics, 2013.
Chang, Ju Young et al., Analysis of Species in Feces, Decreased diversity of the fecal microbiome in recurrent clostridium difficile-associated diarrhea, 2008.
Chassard, C. et al, GI Disease—General, Functional dysbiosis within the gut microbiota of patients with constipated irritable bowel syndrome, 2011.
Chavarri, Maria et al, Drug Delivery, Microencapsulation of a probiotic and prebiotic in alginate- chitosan capsules improves survival in simulated gastro-intestinal conditions, 2010.
Chilton, C.H., et al., "Successful treatment of simulated Clostridum difficile infection in a human gut model by fidaxomicin first line and after vancomycin or metronidazole failure", J Antimicrob Chemother 2014; 69:451-462.
Chisti, Y., "Hydrodynamic Damage to Animal Cells", Critical Reviews in Biotechnology, 21(2):67-110 (2001).
Chitnis, A. et al, C Diff Studies, Epidemiology of community-associated colostridium difficile infection, 2009 through 2011, 2013.
Claaa, E. et al, Analysis of Species in Feces, Performance of the xTAGR Gastrointestinal Pathogen Panel, a Multiplex Molecular Assay for Simultaneous Detection of Bacterial, Viral, and Parasitic Causes of Infectious Gastroenteritis, 2013.
Clabots, C. et al, Strain typing, Development of a rapid and efficient restriction endonuclease analysis typing system for Clostridium difficile and correlation with other typing systems., 1993.
Clarke, S. et al, Microbiome papers, The gut microbiota and it's relationship to diet and obesity, 2012.
Clemente, J. et al, Microbiome papers, The Impact of the Gut Microbiota on Human Health: An Integrative View, 2012.
Cnops, L.; Van Esbroeck, M., Bacterial Preservation via Freezing, Freezing of stool samples improves real-time PCR delection of Entamoeba dispar and Entamoeba histolytica, 2010.
Cody, William et al, Cryopreservation Studies, Skim milk enhances the preservation of thawed -BOC bacterial stocks, 2008.
Cohen, S.H., et al., "Clinical Practice Guidelines for Clostridium difficile Infection in Adults: 2010 Update by the Society for Healthcare Epidemiology of America (SHEA) and the Infectious Diseases Society of America (IDSA)", Infection Control and Hospital Epidemiology, vol. 31, No. 5 (May 2010), pp. 431-455.
Collins, Donald, Bowel disease treatment with FT, Pseudomembranous enterocolitis—further observations on the value of donor fecal enemata as an adjunct in the treatment of pseudomembranous enterocolitis, 1960.
Collins, S. et al, Microbiome papers, The adoptive transfer of behavioral phenotype via the intestinal microbiota: experimental evidence and clinical implications, 2013.
Comito, D.; Romano, C., Pediatrics, Dysbiosis in the Pathogenesis of Pediatric Inflammatory Bowel Diseases, 2012.
Coteur, G., et al., "Evaluation of the meaningfulness of health-related quality of life improvements as assessed by the SF-36 and the EQ-5D Vas in patients with active Crohn's disease", Aliment Pharmacol Ther 29, (2009) 2032-1041.
Cotta, Michael et al, Analysis of Species in Feces, Isolation, characterization and comparison of bacteria from swine faeces and manure storage pits, 2003.
Counting Bacteria, Live/Dead Baclight bacterial viability kits, 2008.
Cox, C.S., "Bacterial Survival in Suspension in Polyethylene Glycol Solutions," J. Gen. Microbiol. 45, 275-281 (1966).
Cox, L.; Blaser, M., Obesity Related, Pathways in Microbe-Induced Obesity, 2013.
Crook, D. et al, C Diff Studies, Fidaxomicin versus vancomycin for Clostridium difficile infection: meta-Analysis of pivotal randomized controlled trials, 2012.
Curtin, Ciara, Analysis of Species in Feces, Researchers examine the genetic diversity of the human gutrnicrobiome, 2012.
D'Agostino, R.B., et al., "Risk Estimation for Recurrent Clostridium Difficile Infection Based on Clinical Factors", Clin. Infect Dis May 2014; 58(10):1386-93.
Dallas, K.B., et al., "Life after colectomy for fulminant Clostridium difficile colitis: a 7-year follow up study", The American Journal of Surgery (2014) 207, 533-539.
Damman, C. et al, FMT Studies and Reviews, The Microbiome and Inflammatory Bowel Disease: Is There aTherapeutic Role for Fecal Microbiota Transplantation?, 2012.
Dan, M et al, Fecal Preservation, Comparison of preservation media and freezing conditions for storage of specimens of faeces, 1989.
David, L. et al, Microbiome papers, Diet rapidly and reproducibly alters the human gut microbiome, 2013.
Davidovics, Z.; Sylvester, F., Ulceratice Colitis, Medical Stool: The Future Treatment for Inflammatory Bowel Disease?, 2013.
De Cruz, P. et al, Analysis of Species in Feces, Characterization of the Gastrointestinal Microbiota in Health and Inflammatory Bowel Disease, 2012.
De Goffau, M. et al, Pediatrics, Fecal Microbiota Composition Differs Between Children With ~—Cell Autoimmunity and Those Without, 2013.
De Leon et al, Ulcerative Colitis, Transient flare of ulcerative colitis after fecal microbiota transplantation for recurrent Clostridium difficile infection, 2013.
De Vrieze, Jop, FMT Studies and Reviews, The Promise of Poop, 2013.
Debast, S.; Bauer, M., Industry, European Society of Clinical Microbiology and Infectious Diseases (ESCMID): update of the treatment guidance document for Clostridium difficile infection {CDI), 2013.
Deshpande, A. et al, Industry, Diagnostic Testing for Clostridium difficile Infection in Patients With Inflammatory Bowel Disease, 2013.
Dethlefsen, L; Reiman, D., Microbiome papers, Incomplete recovery and individualized responses of the human distal gut microbiota to repeated antibiotic perturbation, 2010.

(56) References Cited

OTHER PUBLICATIONS

Deweerdt, S., "A complicated relationship status", Nature, Apr. 17, 2014; 508(7496):S61-3.
Dey, Neelendu et al, GI—General, Association of gut microbiota with post-operative clinical course in Crohn's disease, 2013.
Ding, T., et al., "Dynamics and associations of microbial community types across the human body", Nature, May 15, 2014; 509(7500):357-60.
Dixon, E. et al, Counting Bacteria, Solid-phase microextraction and the human fecal VOC metabolome, 2011.
Dominguez, S.R., et al., "High Colonization Rate and Prolonged Shedding of Clostridium difficile in Pediatric Oncology Patients", Clin Infect Dis, Apr. 29, 2014 (11 pgs.).
Dominguez-Bello et al., "Do you have a probiotic in your future?," Microbes and Infection, vol. 10, pp. 1072-1076 (2008).
Downing, N. et al, Healthcare industry, Clinical Trial Evidence Supporting FDA Approval of Novel Therapeutic Agents, 2005-2012, 2014.
Du Boc, H. et al, GI Disease—General, Connecting dysbiosis, bile-acid dysmetabolism and gut inflammation in Inflammatory bowel diseases, 2013.
Du Boc, H. et al, GI Disease—General, Increase in fecal primary bile acids and dysbiosis in patients with diarrhea predominant irritable bowel syndrome, 2012.
Dubberke, E., "Clostridium Difficile Infection: The Scope of the Problem", Journal of Hospital Medicine, vol. 7, Supp. 3, Mar. 2012, S1-S4.
Dubberke, E.R., et al., "Burden of Clostridium difficile on the Healthcare System", CID 2012:55 {Suppl 2), S88-S92.
Dubberke, ER et al, C Diff Studies, The ecology and pathobiology of clostridium difficile infections: anInterdisciplinary challenge, 2001.
Duleba, K., et al., "Clostridium difficile infection in children hospitalized due to diarrhea", Eur. J_ Clin. Microbiol. Infect. Dis. (2014) 33:201-209.
Dupont, H, Healthcare industry, Diagnosis and management of colostridium difficile infection, 2014.
Dupont, H.L., "Review article: evidence for the role of gut microbiota in irritable bowel syndrome and its potential influence on therapeutic targets", Aliment Pharmacol Ther, May 2014; 39(10):1033-42.
Durban et al., "Assessing Gut Microbial Diversity from Feces and Rectal Mucosa," Microb Ecol., vol. 61, pp. 123-133 (2011).
Durban, Ana et al, GI Disease—General, Instability of the faecal microbiota in diarrhoea-predominant irritable bowel syndrome, 2013.
Durban, Ana et al, GI Disease—General, Structural alterations of faecal and mucosa-associated bacterialcommunities in irritable bowel syndrome, 2012.
Dutta, S.K. et al, FMT Studies and Reviews, Efficacy of Combined Jejunal and Colonic Fecal MicrobiotaTransplantation for Recurrent Clostridium difficile Infection, 2013.
Eckburg, Paul B. et al, Analysis of Species in Feces, Diversity of the Human Intestinal Microbial Flora, 2005.
Ehlermann, P., et al., "Donor fecal transfer for recurrent Clostridium difficile-associated diarrhea in heart transplantation", The Journal of Heart and Lung Transplantation, vol. 33, No. 5, May 2014, 551-553.
Eiseman, B et al, Bowel disease treatment with FT, Fecal Enema as an adjuct in the treatment ofpseudomembranous enterocolitis, 1958.
El Feghal Y, R.E., et al., "Markers of Intestinal Inflammation, Nol Bacerial Burden, Correlate With Clinical Outcomes in Clostridium difficile Infection", Clin Infect Dis. Jun. 2013; 56(12):1713-21.
El-Matary, Wael, Donor Screening, Fecal Microbiots Transplantation: Long-Term Safety Issues, 2013.
Elixhauser, A., et al., "Readmissions following Hospitalizations with Clostridium difficile Infections, 2009", HCUP Statistical Brief #145, Dec. 2012, Agency for Healthcare Research and Quality, Rockville, MD, pp. 1-11.
Elliott, P.; Peakman, T., Industry, The UK Biobank sample handling and storage protocol for the collection, processing and archiving of human blood and urine, 2008.
Emiliani et al., "Comparison of ethylene glycol, 1,2-propanediol and glycerol for cryopreservation of slow-cooled mouse zygotes, 4-cell embryos and blastocysts, Human Reproduction," vol. 15, Issue 4, Apr. 2000, pp. 905-910.
Eyre, David et al, C Diff Studies, Diverse Sources of C. difficile Infection Identified on Whole-Genome Sequencing, 2013.
Eyre, David et al, C Diff Studies, Predictors of first recurrence of clostridium difficile infection: implications for initial management, 2012.
Falony, Get al, Cryopreservation Studies, Coculture fermentations of bifidobacterium species and bacteroides thetaiotaomicron reveal a mechanistic insight into the prebiotic effect of inulin-type fructans, 2009.
Fava, F.; Danese, S., GI Disease—General, Intestinal microbiota in inflammatory bowel disease: friend or foe?, 2011.
Floch, Martin, C Diff Treatment with Fecal Transplant, Fecal bacteriotherapy, fecal transplant and the microbiome, 2010.
Flores, R. et al, Analysis of Species in Feces, Assessment of the human faecal microbiota: II. Reproducibility and associations of 16S rRNA pyrosequences, 2012.
Flotterod et al., "Refractory Clostridium difficile infection," Untraditional treatment of antibiotic- induced colitis, Tidsskr Nor Laegeforen, vol. 111, No. 11, pp. 1364-1365, Norwegian. PMID: 2042156. (Apr. 1991).
Food and Drug Administration, "Small Business Guide to FDA", 2011 (28 pgs.).
Fox, Jeffery, General FMT News and Regulations, Fecal transplants to follow FDA rules, 2013.
Franks, Alison et al, Analysis of Species in Feces, Variations of Bacterial Populations in Human Feces Measured by Fluorecent In Situ Hybridization with Group-Specific 16S rRNA-Targeted Oligonucleotide Probes, 1998.
Frantzen, M. et al, Microbe preservation, Emperical evaluation of preservation methods for faecal DNA, 1998.
Freeman, J.; Wilcox, M.H., Microbe preservation, The effects of storage conditions on viability of Clostridium difficile vegetative cells and spores and toxin activity in human faeces, 2003.
Fridkin, S., et al., "Vital Signs: Improving Antibiotic Use Among Hospitalized Patients", MMWR, Mar. 7, 2014, vol. 53, No. 9, 194-200.
Friedman, ND et al, C Diff Studies, Prevalence of colostridium difficile colonization among healthcare workers, 2013.
Friedman-Morago, R.J. et al, FMT Studies and Reviews, Fecal Microbiota Transplantation for Refractory Clostridium difficile Colitis in Solid Organ Transplant Recipients, 2014.
Garborg et al., "Results of faecal donor instillation therapy for recurrent Clostridium difficile- associated diarrhoea," Scandinavian Journal of Infectious Diseases, vol. 42, pp. 857-886 (2010).
Gareau, M; Barrett, K., Gut Microbiome News, Fluid and electrolyte secretion in the inflamed gut: Novel targets for treatment of inflammation induced diarrhea, 2013.
Gasol, Joseph et al, Counting Bacteria, Using flow cytometry for counting natural planktonic bacteria andUnderstanding the structure of planktonic bacterial communities, 2000.
Gerding, D.N., "Global Epidemiology of Clostridium difficile Infection in 2010", Infection Control and Hospital Epidemiology, 2010, vol. 31, No. S1, pp. S32, S34.
Gewolb, Ira et al, Analysis of Species in Feces, Stool microflora in extremely low birthweight infants, 1999.
Giniatullina, A. et al., Industry, Building for Big Pharma, 2013.
Gomez-Simmons, A. et al, C Diff Studies, Comparison of 3 severity criteria for colostridium difficile infection, 2014.
Goodman, Andrew et al, Analysis of Species in Feces, Extensive Personal Human Gut Microbiota CultureCollections Characterized and Manipulated in Gnotobiotic Mice, 2011.
Gophna, Uri, Microbiome papers, The guts of dietary habits, 2011.
Gravitz, L, Microbiome papers, The critters within, 2012.
Green, H. et al, Microbe preservation, Impact of Freezing on the Future Utility of Archived Surveillance Culture Specimens, 2007.
Grzeskowiak, L. et al, Pediatrics, Distinct Gut Microbiota in Southeastern African andNorthern European Infants, 2011.

(56) References Cited

OTHER PUBLICATIONS

Guarner, J., et al., "Correlation of the detection of Clostridium difficile toxins in stools and presence of the clostridia in tissues of children", Human Pathology (2010) 41, 1586-1592.
Gueimonde, M. et al, Analysis of Species in Feces, New real-lime quantitative PCR procedure for quantification of bifidobacleria in human fecal samples, 2004.
Guerrero, D.M et al, C-Diff Studies, Asymptomatic carriage of toxigenic ClostridiumDifficile by hospitalized patients, 2013.
Guillemin, I. et al, C Diff Studies, Patients' Experience and Perception of Hospital- TreatedClostridium difficile Infections: a Qualitative Study, 2014.
Guo, B., et al., "Systematic review: faecal transplantation for the treatment of Clostridium difficile-associated disease", Aliment Pharmacol. Ther. 2012; 35:865-875.
Gupta, A. et al, Drug Delivery, Design and development of liposomes for colon targeted drug delivery, 2013.
Gupta, A., et al., "Community-acquired Clostridium difficile infection: an increasing public health threat", Infection and Drug Resistance 2014:7 63-72.
Gut Microbiome News, Articles highlight advances, potential applications of gut microbiome research, 2012.
Gut Microbiome News, Consortium members publish collection of studies stemming from human microbiome project, 2005.
Gut Microbiome News, Structure, function and diversity of the healthy human microbiome, 2012.
Gutierrez, R. et al, C Diff Studies, Epidemiology of Clostridium Difficile infection among active duty United States military personnel (1998-2010), 2013.
Haines, RB, Bacterial Presentation via Freezing, The effect of freezing on bacteria, 1938.
Halabi, W. et al, C Diff Studies, Colostridium Difficile colitis in the united states: a decade of trends, outcomes, risk factors for colectomy, and mortality after colectomy, 2013.
Hamil Ton, Matthew et al., Bacterial Presentation via Freezing, Standardized frozen preparation for transplantation of fecal microbiota for recurrent clostridium difficile infection, 2012.
Hamil Ton, Matthew et al, Bacterial Preservation via Freezing, High-throughput DNA Sequence Analysis Reveals a Stable Engraftment of Gut Microbiota Following Transplantation of Previously Frozen Fecal Bacteria, 2013.
Hansen, R. et al, Pediatrics, Microbiota of De-Novo Pediatric IBD: Increased Faecalibacterium Prausnitzii and Reduced Bacterial Diversity in Crohn's But Not in Ulcerative Colitis, 2012.
Hao, W.; Lee, Y., Microbiome papers, Microflora of the Gastrointestinal Tract, 2004.
Harmsen, Hjm et al, Analysis of Species in Feces, Comparison of viable cell counts and fluorscent in situhybridization using specific rRNA-based probes for the quantification of human fecal bacteria, 1999.
Harpe, S.E., et al., "Characterization of Continued Antibacterial Therapy After Diagnosis of Hospital-Onset Clostridium difficile Infection: Implications for Antimicrobial Stewardship", Pharmacotherapy, vol. 32, No. 8, 2012, pp. 744-754.
Hawes, R.H., et al., "A consensus document on bowel preparation before colonoscopy: Prepared by a Task Force From The American Society of Colon and Rectal Surgeons (ASCRS), the American Society for Gastrointestinal Endoscopy (ASGE), and the Society of American Gastrointestinal and Endoscopic Surgeons (SAGES)", Gastrointestinal Endoscopy, vol. 63, No. 7, 2006, 894-910.
Hecht, GA et al, Industry, What's the Value of an Fda Ind for Fecal Microbiota Transplantation in Clostridium difficile Infection?, 2013.
Hedge et al., "New advances in the treatment of Clostridium difficile infection (CDI)," Therapeutics and Clinical Risk Management 4(5) pp. 949-964 (2008).
Hellemans et al., "Fecal transplantation for recurrent Clostridium difficile colitis, an underused treatment modality," Acta Gastro-Enterologica Belgica vol. IXXII (Apr.-Jun. 2009).
Hennequin, C., et al., "GroEL (Hsp60) of Clostridium difficile is involved in cell adherence", Microbiology (2001), 147, 87-96.

Henning, Torsten, Industry, Polyethylene glycols (PEGs) and the pharmaceutical industry, 2002.
Henry-Stanley et al., "Polyethylene Glycol Influences Microbioal Interactions with Intestinal Epithelium," Shock, vol. 31, No. 4, pp. 390-396, (2009).
Hensgen, M.P.M., et al., "Time interval of increased risk for Clostrium difficile infection after exposure to antibiotics", J Antimicrob Chemother 2012; 67:742-748.
Hill, M.J. et al, Analysis of Species in Feces, The normal chronic bacterial flora, 1975.
HMPC {Multiple Authors), Microbiome papers, Structure, function and diversity of the healthy human microbiome, 2012.
Hoefman, Microbe preservation, Survival or Revival: Long-Term Preservation Induces a Reversible Viable but Non-Culturable State in Methane-Oxidizing Bacteria, 2012.
Hoffman, Christian, Microbe papers, The human intestinal microbiome and dietary patterns, 2011.
Hoffmann, Christian et al, Analysis of Species in Feces, Archaea and Fungi of the Human Gut Microbiome: Correlations with Diel and Bacterial Residents, 2013.
Holy, Ondrej et al, C Diff Studies, Oxygen tolerance in anaerobic pathogenic bacteria, 2012.
Honda, H.; Dubberke, E., C Diff Studies, The changing epidemiology of Clostridium difficile infection, 2014.
Hoover, D; Rodriguez-Palacios, A., C Diff Studies, Transmission of colostridium difficile in foods, 2013.
Hopkins, M. J., et al., Variation in human intestinal microbiota with age, Digest Liver Dis 2002; 34{Suppl2):S12-8.
Hourigan, S.K., et al., "The Prevalence of Clostridium difficile Infection in Pediatric and Adults Patients withInflammatory Bowel Disease", Dig Dis Sci May 1, 2014, DOI: 10.1007/s10620-0143169-4 (6 pgs.).
Hsiao, E. et al, Microbiome papers, Microbiota Modulate Behavioral and Physiological Abnormalities Associated with Neurodevelopmental Disorders, 2013.
Hu, MY., et al., "Prospective Derivation and Validation of a Clinical Prediction Rule for Recurrent Clostridium difficile Infection", Gastroenterology 2009; 136:1206-1214.
Huang, Yet al, Drug Delivery, A novel plug-controlled colon-specific pulsatile capsule with tablet of curcumin-loaded SMEDDS, 2013.
Hubalek, Zdenek, Cryopreservation Studies, Protectants used in the cryopreservation of microorganisms, 2002.
Humphreys, D.P., et al., "Antibodies for the treatment of Clostridium difficile infection", Clin Vaccine Immunol. Apr. 30, 2014, doi:10.1128/CVI.00116-14 (35 pgs.).
Iida, N. et al, Cancer, Supplimentary Materials for Commensal Bacteria Control Cancer Response to Therapy by Modulating the Tumor Microenvironment, 2013.
Jakobbsson, Hedvig et al, Microbiome papers, Short-Term Antibiotic Treatment Has Differing Long-Term Impacts on the Human Throat and Gut Microbiome, 2010.
Jakobsson, Hedvig et al, Gut Microbiome News, Decreased gut microbiota diversity, delayed Bacteroidetes colonisation and reduced Th1 responses in infants delivered by Caesarean section, 2013.
Jansson, Janet, GI Disease—General, Microbiota and Inflammatory Bowel Disease (presentation), 2011.
Jeffery, I. et al, GI Disease—General, An irritable bowel syndrome subtype defined by species-specific alterations in faecal microbiota, 2013.
Jernberg, C. et al, Microbiome papers, Long-term ecological impacts of antibiotic administration on the human intestinal microbiota, 2007.
Jiang, z. et al, C Diff Studies, Physician Attitudes Toward the Use of Fecal Transplantation for Recurrent Clostridium difficile Infection in a Metropolitan Area, 2013.
Johnson, S., et al., "Fidaxomicin "Chaser" Regimen Following Vancomycin for Patients With Multiple Clostridium difficile Recurrences", Clin Infect Dis. Jan. 2013; 56(2):309-10.
Jones, A.M., et al., "Clostridium difficile: A European perspective", J Infect (2012), http://dx.doi.org/10.1016/j.inf.2012.10.019, pp. 1-14.

(56) References Cited

OTHER PUBLICATIONS

Jump, R. et al, C Diff Studies, Tigecycline Exhibits Inhibitory Activity against Colostridium difficile in the colon of Mice and does not promote growth or toxin production, 2013.
Kaaskoush, N. et al, Pediatrics, Chrohn's, Microbial Dysbiosis in Pediatric Patients with Crohn's Disease, 2012.
Kahn, S. et al, Pediatrics, Colonoscopic fecal microbiota transplant for recurrent colostridium difficile infection in a child, 2012.
Kahn, S. et al, Ulcerative Colitis, Fecal Bacteriotherapy for Ulcerative Colitis: Patients Are Ready, Are We?, 2012.
Kahn, S.A., et al., "Colonoscopic Fecal Microbiota Transplant for Recurrent Clostridium difficile Infection in a Child", The American Journal of Gastroenterology, vol. 107, Dec. 2012, 1930-1931.
Kahn, S.A., et al., "Fecal Bacteriotherapy for Ulcerative Colitis: Patients Are Ready, Are We?", Inflamm Bowel Dis. Apr. 2012; 18(4):676-684.
Kao, D., et al., "Fecal Microbiola Transplantation Inducing Remission in Crohn's Colitis and the Associated Changes in Fecal Microbial Profile", J Clin Gastroenlerol, 2014, PMID: 24667590 (4 pgs.).
Karadsheh, Z.; Sule, S., C Diff Treatment with Fecal Transplant, Fecal transplantation for the treatment of recurrent colostridium difficile infection, 2013.
Karlsson, F. et al, Microbiome papers, Gut metagenome in European women with normal, impaired and diabetic glucose control, 2013.
Karmali, S. et al, Industry, GAGS Clinical Practice Committee report: the science of Clostridium difficile and surgery, 2013.
Kassam, Z., et al., "Fecal Microbiota Transplantation for Clostridium difficile Infection: Systematic Review and Meta Analysis", Am J Gastroenterol Mar. 19, 2013; doi: 10.1038/ajg.2013.59, pp. 1-9.
Kassam, Zain et al, C Diff Treatment with Fecal Transplant, Fecal microbiolia transplantation for clostridium difficile infection: systematic review and meta-analysis, 2013.
Kassam, Zain et al, C Diff Treatment with Fecal Transplant, Fecal transplant via retention enema for refractory or recurrent clostridium difficile infection, 2012.
Kassam, Zain et al, Donor Screening, Navigating long-term safety in fecal microbiota transplantation, 2013.
Keller, J.; Surawicz, C., C Diff Studies, Clostridium difficile Infection in the Elderly, 2014.
Keller, J.M., et al., "Clostridium difficile Infection in the Elderly", Clin. Geriatr Med 30 (2014) 79-93.
Kellerma Yer, Richard, Pediatrics, Prospects and challenges for intestinal microbiome therapy in pediatricgastrointestinal disorders, 2013.
Kelly, C. et al, Industry, A How to Guide: investigational New Drug Application for Fecal Microbiota Transplantation, 2013.
Kelly, Colleen, Healthcare industry, FDA's role in regulating FMT is imperative, 2013.
Kelson, J.; Wu, G., Microbiome papers, The gut microbiota, environment and diseases of modem society, 2012.
Khanna, S., et al., "Clostridium difficile infection: management strategies for a difficult disease", Ther Adv Gastroenterol 2014, vol. 7(2) 72-86.
Khanna, S.; Tosh, P., Industry, A Clinician's Primer on the Role of the Microbiome in Human Health and Disease, 2014.
Khortus, Alexander et al., Analysis of Species in Feces, Changes in the composition of the human fecal microbiome after bacleriotherapy for recurrent clostridium difficile associated diahrrea, 2010.
Khortus, Alexander et al, C Diff Treatment with Fecal Transplant, Therapeutic transplantation of the distal gut microbiome, 2010.
Killgore, G. et al, Strain typing, Comparison of Seven Techniques for Typing International Epidemic Strains of clostridium difficile: Restriction Endonuclease Analysis, Pulsed-Field Gel Electrophoresis, PCR-Ribotyping, Multilocus Sequence Typing, Multilocus Variable-Number Tandem-Repeat Analysis, Amplified Fragment Length Polymorphism, and Surface Layer Protein A Gene Sequence Typing, 2008.

Kim, B. et al, Microbiome papers, Current status and future promise of the human microbiome, 2013.
Kim, J., "Editorial Commentary: 'High Colonization Rate and Prolonged Shedding of Clostridium difficile in Pediatric Oncology Patients'", Clinical Infectious Diseases Advance Access, 2014 (6 pgs.).
Kim, J., et al., "Epidemiological Features of Clostridium difficile-Associated Disease Among Inpatients at Children's Hospitals in the United States, 2001-2006", Pediatrics 2008; 122:1266-1270.
Klein, E.J., et al., "Diarrhea Etiology in a Children's Hospital Emergency Department: A Prospective Cohort Study", Clin Infect Dis., Oct. 1, 2006; 43(7):807-13.
Knetsch, C.W. et al, Strain typing, Current application and future perspectives of molecular typing methods to study clostridium difficile infections, 2013.
Koboziev, I. et al, Microbiome papers, Role of the Enteric Microbiota in Intestinal Homeostasis and Inflammation, 2013.
Koeth, R. et al, Microbiome papers, Intestinal microbiota metabolism of 1-camiline, a nutrient in red meal, promotes atherosclerosis, 2013.
Konkel, Lindsey, Microbiome papers, The environment within: exploring the role of the gut microbiome in health and disease, 2013.
Konstantinov, S. Peppelenbosch, M., FMT Studies and Reviews, Fecal Microbiota Transfer May Increase Irritable Bowel Syndrome and Inflammatory Bowel Diseases-Associated Bacteria, 2013.
Kootte, R. et al, Obesity Related, The therapeutic potential of manipulating gut microbiota in obesity and type 2 diabetes mellitus, 2012.
Korpela, K., et al., "Gut microbiota signatures predict host and microbiota responses to dietary interventions in obese individuals", PLOS ONE, Mar. 2014, vol. 9, Issue 3, e90702 (10 pgs.).
Kozak, G.K., et al., "Antimicrobial Resistance in *Escherichia coli* Isolates from Swine and Wild Small Mammals in the Proximity of Swine Farms and in Natural Environments in Ontario, Canada", Applied and Environmental Microbiology, reb. 2009, p. 559-566.
Kristjansson, M. et al, Strain typing, Comparison of Restriction Endonuclease Analysis, Ribotyping, and Pulsedrield Gel Electrophoresis for Molecular Differentiation of Clostridium difficile Strains, 1994.
Kuk, S. et al, Microbial Preservation, Stool sample storage conditions for the preservation of Giardia intestinalis DNA, 2012.
Kumar, P. et al, Pediatrics, Comparative analysis of fecal microflora of healthy full-term Indian infants born with different methods of delivery {vaginal vs cesarean): *Acinetobacter* sp. prevalence in vaginally born infants, 2012.
Kump, Patrizia, et al, Ulcerative Colitis, Alteration of intestinal dysbiosis by fecal microbiota transplantation does not induce remission in patients with chronic active uncerative colitis, 2013.
Kunde, S. et al, Pediatrics, Safety, Tolerability, and Clinical Response After Fecal Transplantation in Children and Young Adults With Ulcerative Colitis, 2013.
Kyne, Lorraine et al, C Diff Studies, Asymptomatic carriage of clostridium difficile and serum levels of lgG antibody against toxin A, 2000.
L Awley, T.D., et al., "Intestinal colonization resistance", Immunology, Jan. 2013; 138(1 ): 1-11.
Lagier, J_ et al, Microbiome papers, Microbial culturomics: paradigm shift in the human gut microbiome study, 2012.
Laksminarayana, B. et al, Analysis of Species in Feces, Prevalence and characterization of Clostridiumperfringens from the faecal microbiota of elderly Irish subjects, 2013.
Landy, J. et al, FMT Studies and Reviews, Review article: faecal transplantation therapy for gastrointestinal disease, 2011.
Larson, H.E., et al., "Epidemiology of Clostridium difficile in infants", J Infect Dis., Dec. 1982;146(6):727-33.
Lee, C., et al., "The outcome and long-term follow-up of 94 patients with recurrent and refractory Clostridium difficile infection using single to multiple fecal microbiota transplantation via retention enema", Eur J_ Clin Microbiol Infect Dis., J014 Mar. 14 (4 pgs.).
Lee, S.M et al, Gut Microbiome News, Bacterial colonization factors control specificity and stability of the gut microbiota, 2013.

(56) References Cited

OTHER PUBLICATIONS

Lemon, Katherine, Microbiome papers, Microbiola-Targeled Therapies: An Ecological Perspective, 2012.
Ley, R., "The sweet tooth of Clostridium difficile", Nature Medicine, vol. 20, No. 3, Mar. 2014, 248-49.
Liao, CH et al, Bacterial Survival in different soln, Survivability and long-term preservation of bacteria in water and in phosphate-buffered saline, 2002.
Lichtman, J_ et al, Microbiome papers, Host-centric proteomics of stool: a novel strategy focused on intestinal responses to the gut microbiota, 2013.
Lin, HJ. et al, C Diff Studies, Risk factors for colostridium difficile associated diarrhea among hospitalized adults with fecal toxigenic C. difficile colonization, 2013.
Liu, Z.; Cao, A.; Cong, Y.,Microbiome papers, Microbiota regulation of inflammatory bowel disease and colorectal cancer, 2013.
Lo Vecchio, A; Cohen, M., Fmt Studies and Reviews, Fecal microbiola transplantation for Clostridium difficile infection: benefits and barriers, 2013.
Lofland, D., et al., "Fecal Transplant for Recurrent Clostridium difficile Infection", Clin Lab Sci., 2013, 26(3):131-5.
Lopetuso, L.R., et al., "Commensal Clostridia: leading players in the maintenance of gut hemostasis", Gut Pathogens, 2013, 5:23 (8 pgs.).
Louie, T. et al, C Diff Studies, Fidaxomicin Preserves the Intestinal Microbiome During and After Treatment of clostridium difficile Infection {CDi) and Reduces Both Toxin Reexpression and Recurrence of CDi, 2012.
Lowy, I. et al, C Diff Studies, Treatment with Monoclonal Antibodies against Colostridium difficile Toxins, 2010.
Lozupone, C. et al, Microbiome papers, Diversity, stability and resilience of the human gut microbiota, 2012.
Lucado, J., et al., "Clostridium difficile Infections (COi) in Hospital Stays, 2009", HCUP Statistical Brief#124, Jan. J012. Agency for Healthcare Research and Quality, Rockville, MD http:www.hcupus.ahrg.gove/reports/statbriefs/sb124.pdf, pp. 1-12.
Macconnachie et al., Faecal transplant for recurrent Clostridium difficile-associated diarrhoea: a UK case series, Q J Med vol. 102 pp. 781-784 (2009).
MacFarland, Lynne et al, C Diff Studies, Recurrent clostridium difficile disease: epidemiology and clinicalcharacteristics, 1999.
MacNeal, Ward et al, Analysis of Species in Feces, The fecal bacteria of health men, 1909.
Manges, A. et al, Microbiome papers, Comparative metagenomic study of alterations to the intestinal microbiota and risk of nosocomial colostridium difficile-associated disease, 2010.
Manichanh et al., "Reshaping the gut microbiome with bacterial transplantation and antibiotic intake," Genome Research, vol. 20, pp. 1411-1419 (2010).
Marcille, J. (editor), FMT Studies and Reviews, Fecal Microbiota Transplantation for Treating Recurrent Clostridium difficile Infection, 2013.
Martin, J., et al., "Clostridium difficile: biological therapies", Curr Opin Infect Dis., Oct. 2013; 26(5):454-60.
Martin-Dejardin, F. et al, Drug Delivery, A way to follow the viability of encapsulated Bifidobacterium bifidum subjected to a freeze-drying process in order to target the colon: Interest of flow cytometry, 2013.
Martinez, I. et al, Microbiome papers, Long-term temporal analysis of the human fecal microbiota revealed a stable core of dominant bacterial species, 2013.
Martinez, J.A., et al., "Role of dietary polyphenols and inflammatory processes on disease progression mediated by the gut microbiota", Rejuvenation Res., Oct. 2013; 16(5):435-7.
Mattila, E et al, C Diff Treatment with Fecal Transplant, Fecal transplantation, though colonoscopy, is effective therapy for recurrent clostridium difficile infection, 2012.
Maturin, Larry et al, Counting Bacteria, Bacteriological analytical manual chap 3: aerobic plate count, 2001.

Maukonen, J_ et al, Analysis of Species in Feces, The currently used commercial DNA-extraction methods give different results of clostridial and actinobacterial populations derived from human fecal samples, 2011.
McCune, V.L., et al., "Faecal transplantation for the treatment of Clostridium difficile infecton: a review", Int J Antimicrob Agents, Mar. 2014; 43(3):201-6.
McDonald, C. et al, C Diff Studies, Colostridium difficile infection in patients discharged from U.S. short-stay hospitals, 1996-2003, 2006.
Mellow, M.H., et al., "Colonscopic Fecal Bacteriotherapy in the Treatment of Recurrent Clostridium Difficile Infection Results and Follow-up", OSMA Journal, Mar. 2011, pp. 89-91.
Merlino, J_ et al, Agar Plate Info, Evaluation of CHROMagar Orientation for differentiation and presumptiveidentification of Gram negative bacilli and Enterococcus species., 1996.
Minot, S. et al, Analysis of Species in Feces, Rapid evolution of the gut virome, 2013.
Mitchell, B. G., et al., "The prolongation of length of stay because of Clostridium difficile infection", American Journal of Infection Control 42 (2014) 164-7.
Mitchell, M., "Determining Criticality-Process Parameters and Quality Attributes Part I: Criticality as a Continuum", BioPharam, Dec. 1, 2013, (7 pgs.).
Mitchell, M., "Determining Criticality-Process Parameters and Quality Attributes Part II; Design of Experiments and Data-Driver Criticality", BioPharam, Jan. 1, 2014, (9 pgs.).
Moayyedi, P., et al., "Canadian Association of Gastroenterology position statement: Fecal microbiota transplant therapy", Can J Gastroeneterol Hepatol, vol. 28, No. 2, Feb. 2014 (3 pgs.
Mole, Beth, Industry, FDA gets to grips with Faeces, 2013.
Momozawa, Y. et al, Analysis of Species in Feces, Characterization of Bacteria in Biopsies of Colon and Stools by High roughput Sequencing of the V2 Region of Bacterial 16S rRNA Gene in Human, 2011.
Moore, Wec et al, Analysis of Species in Feces, Human fecal flora: the normal flora for 20 Japanese-Hawaiians, 1974.
Moschen, A. et al, Microbiome papers, Dietary Factors: Major Regulators of the Gut's Microbiota, 2012.
Mueller et al., "Differences in Fecal Microbiota in Different European Study Populations in Relation to Age, Gender, and Country: A Cross-Sectional Study," Applied and Environmental Microbiology, vol. 72, No. 2, pp. 1027-1033 (2006).
Mukhopadhyay, S.; Linstedt, A., Microbiome papers, Manganese Blocks Intracellular Trafficking of Shiga Toxin and Protects Against Shiga Toxicosis, 2012.
Multiple articles, Agar Plate Info, Anaerobic Bacteriology, 2007.
Multiple pharma companies, Industry, Rare Diseases: A report on orphan drugs in the pipline, 2013.
Munukka, E. et al, Microbiome papers, Women With and Without Metabolic Disorder Differ in Their Gut Microbiota Composition, 2012.
Murri, M. et al, Pediatrics, Gut microbiota in children with type 1 diabetes differs from that in healthy children: a case- control study, 2013.
Nagaro, K.J., et al., "Non-Toxigenic Clostridium difficile Protects Hamsters Against Challenge with Historic and Epidemic Toxigenic BI/NAP1/027 C. difficile", Antimicrob Agens Chemother. Nov. 2013;57(11 ):5266-70.
Nature Publishing Group, Industry, Recent patent applications in bacleriotherapy, 2013.
Navidad, J_ et al, Donor Screening, Evaluation of Luminex xTAG gastrointestinal pathogen analyte specific reagents or high throughput, simultaneous detection of bacteria, viruses, and parasites of clinical and public health importance, 2013.
Neir, T. et al, Analysis of Species in Feces, Stool microbiome and metabolome differences between colorectal cancer patients and healthy adults, 2013.
Nieuwdorp, Max, Microbiome papers, Gut microbiota determine insulin sensitivity, 2013.
Nitzan, 0. et al, Industry, Clostridium difficile and inflammatory bowel disease: Role in pathogenesis and implications in treatment, 2013.

(56) References Cited

OTHER PUBLICATIONS

Noverr, M.; Huffnagle, G., Microbiome papers, Does the microbiota regulate immune responses outside the gut?, 2004.
Numata, K., et al., "Silk-based delivery systems of bioactive molecules", Adv Drug Deliv Rev. Dec. 30, 2010; 62 (15):1497-1508.
Nyangale, E. et al, Microbiome papers, Gut Microbial Activity, Implications for Health and Disease: The Potential Role of Metabolite Analysis, 2012.
Nylund, C.M., et al., "Clostridium difficile Infection in Hospitalized Children in the United States", Arch Pediatr Adolesc Med 2011;165(5):451-457.
O'Hara, Ann et al, Gut Microbiome News, The gut flora as a forgotten organ, 2006.
O'Horo, J.C., et al., "Treatment of recurrent Clostridium difficile infection: a systematic review", Infection (2014) 12:43-59.
O'Sullivan, O. et al, Microbiome papers, Alterations in intestinal microbiota of elderly Irish subjects post-antibiotic therapy, 2013.
O'Toole, P.W., Microbiome papers, Changes in the intestinal microbiota from adulthood through old age, 2012.
Ohkusu, K., et al., "Cost-Effective and Rapid Presumptive Identification of Gram-Negative Bacilli in Routine Urine, Pus, and Stool Cultures: Evaluation of the Use of CHROMagar Orientation Medium in Conjunction with Simple Biochemical Tests", Journal of Clinical Microbiology, Dec. 2000, vol. 38, No. 12, p. 4586-4592.
Ohtake, S. et al, Microbiome papers, Formulation and Stabilization of Francisella tularensis Live Vaccine Strain, 2011.
Oldfield, E.C., et al., "Clinical update for the diagnosis and treatment of Clostridium difficile infection", World J Gastrointest Pharacol Ther, Feb. 6, 2014; 5(1): 1-26.
Olle, Bernal, Microbiome papers, Medicines from microbiola, 2013.
Olson, Mary et al, C Diff Treatment with Fecal Transplant, 10 years of prospective clostridium difficile associated disease surveillance and treatment at the Minneapolis VA medical center, 1994.
Onneby, K. et al, Cryopreservation Studies, Effects of di- and polusaccharide formulations and storage conditions on survival of freeze-dried sphingobium, 2013.
Onouchi, S. et al, Cancer, PCR-based Assessment of the Recovery Rate of Exfoliated Colonocytes or Cancer Cells from Fecal Samples Depends on the Storage Conditions after Defecation, 2007.
Orenstein, R.; Griesbach, C.; DiBaise, J., General FMT News and Regulations, Moving fecal microbiotatransplantation into the mainstream, 2013.
Ott, Stephan et al, Microbial Preservation, In vitro alterations of intestinal bacterial micribiota in fecal samples though storage, 2004.
Ott, Stephen et al, Analysis of Species in Feces, Quantification of Intestinal Bacterial Populations by Real-Time PCR with a Universal Primer Set and Minor Groove Binder Probes: A Global Approach to the Enteric Flora, 2004.
Owens, C. et al, Donor Screening, Fecal microbiota transplantation and donor standardization, 2013.
Pamer, E.G., FMT Studies and Reviews, Fecal microbiota transplantation: effectiveness, complexities, and lingering concerns, 2014.
Papa, E. et al, Pediatrics, Non-Invasive Mapping of the Gastrointestinal Microbiota Identifies Children with Inflammatory Bowel Disease, 2012.
Parekh, P.J., et al., "The role and influence of gut microbiota in pathogenesis and management of obesity and metabolic syndrome", Front Endocrinol (Lausanne), Apr. 7, 2014; 5:47 (7 pgs.).
Pascarella, F., et al., "Impact of Clostridium difficile infection on pediatric inflammatory bowel disease", J Pediatr. Jun. 2009; 154(6):854-8.
Patel, L.N., et al., "Fecal transplantation therapy for Clostridium difficile—associated pouchitis", Int J Colorectal Dis (2014) 29:263-264.
Patel, N. et al, FMT Studies and Reviews, Fecal Microbiota Transplant for Recurrent Colostridium difficile Infection: Mayo Clinic in Arizona Experience, 2013.
Paterson, David et al, Bowel disease treatment with FT, Pulling back the bugs: bacterial treatment relieves chronic diarrhea, 1994.
Pathak, et al, FMT Studies and Reviews, Treatment of relapsing Clostridium difficile infection using fecal microbiota transplantation, 2013.
Pennisi, E., Cancer, Cancer therapies use a little help from microbial friends, 2013.
Perez-Chanona, E., et al., "From promotion to management: The wide impact of bacteria on cancer and its treatment", Bioessays, Apr. 22, 2014 (7 pgs.).
Persky et al., "Treatment of Recurrent Clostridium difficile—Associated Diarrhea by Administration of Donated Stool Directly Through a Colonoscope," The American Journal of Gastroenterology, vol. 95, No. 11 (2000).
Peterson, B et al, Centrifugation, Bacterial Cell Surface Damage due to Centrifugal Compaction, 2012.
Petrof, Khoruls, Microbiome papers, From Stool Transplants to Next-generation Microbiola Therapeutics, 2014.
Pierce, K., "Physician Induced CRE Infections", 2014, Hardy Diagnostics (4 pgs.).
Pisano, R. et al, Industry, Quality by design: scale-up of freeze-drying cycles in the pharmaceutical industry, 2013.
Planche, T.D., et al., "Differences in Outcome According to Clostridium difficile Testing Method: A Prospective Multicentre Diagnostic Validation Study of C difficile Infection", Lancet Infect Dis. Nov. 2013.; 13(11):936-45.
Plate Info, BBL CDC Anaerobe 5% Sheep Blood Agar, 2006.
Postgate, Jr et al, Bacterial Presentation via Freezing, On the survival of frozen bacteria, 1961.
Pray, L.; Pillsbury, L.; Tomayko, E., Microbiome papers, The human microbiome, diet and health, 2013.
Preheim, S.P., et al., "Computational Methods for High-Throughput Comparative Analyses of Natural Microbial Communities", Methods Enzymol. 2013; 531:354-70.
Prideaux, L. et al, GI Disease—General, Inflammatory bowel disease in Asia: A systemic review, 2012.
Proom, H. et al, Bacterial via Freezing, The drying and preservation of bacterial cultures, 1948.
Qa'Dan, M., et al., "pH-induced conformational changes in Clostridium difficile toxin B", Infect Immun., May 2000; 68 5):2470-4.
Qin, J. et al, Microbiome papers, A metagenome-wide association study of gut miocrobiota in type 2 diabetes, 2012.
R. Satokari et al., "Simple faecal preparation and efficacy of frozen inoculum in faecal microbiota transplantation for recurrent Clostridium difficile infection—an observational cohort study," Alimentary Pharmacology & Therapeutics, vol. 11, No. 1, Oct. 29, 2014, pp. 46-53.
Rao, A., et al., "In Vitro Killing of Nosocomial Pathogens by Acid and Acidified Nitrite", Antimicrob. Agents Chemother. 2006, 50(11 ): 3901-3904.
Rechner, Paula et al, C Diff Studies, Clinical Features of Clostridil Bacteremia: A review from a rural area, 2001.
Reynolds, Jackie, Agar Plate Info, Serial Dilution Protocol ASM, 2012.
Ridaura, V. et al, Obesity Related, Gut microbiota from twins discordant for obesity modulate metabolism in mice, 2013.
Ridlon, J.M. et al, Microbiome papers, Cirrhosis, bile acids and gut microbiota. Unraveling a complex relationship, 2013.
Ringel, Y., et al., "The Intestinal Microbiota and Immune Function in the Pathogenesis of Irritable Bowel Syndrome", Am J Physiol Gastrointest Liver Physiol, Oct. 15, 2013; 305(8):G529-41.
Rinttila, T. et al, Analysis of Species in Feces, Development of an extensive set of 16S rDNA- targeled primers for quantification of pathogenic and indigenous bacteria in faecal samples by real-lime PCR, 2004.
Roesch et al., "Influence of Fecal Sample Storage on Bacterial Community Diversity," The Open Microbiology Journal, 3, pp. 40-46 (2009).
Roesch, L. et al, Microbial Preservation, Influence of fecal sample storage on bacterial community diversity, 2009.
Rogler, G., et al., "The heart and the gut", Eur Heart J, Feb. 2014; 35(7):426-30.
Rohlke, F., et al., "Fecal microbiota transplantation in relapsing Colostridium difficile infection", Therap AdvGastroenterol., Nov. 2012; 5(6):403-20.

(56) References Cited

OTHER PUBLICATIONS

Rolfe, R et al, Analysis of Species in Feces, Bacterial interference between clostridium difficile and normal fecal flora, 1981.
Rubin, D. et al, GI Disease—General, Chronic intestinal inflammation: inflammatory bowel disease and colitis-associated colon cancer, 2012.
Rubin, David, Ulcerative Colitis, Curbing our enthusiasm for fecal transplantation in ulcerative colitis, 2013.
Rubin, T.A., et al., "Fecal microbiome transplantation for recurrent Clostridium difficile infection: Report on a case series", Anaerobe 19 (2013) 22-26.
Russell, G. et al, FMT Studies and Reviews, Fecal bacteriotherapy for relapsing colostridium difficile infection in a child: a proposed treatment protocol, 2010.
Safdar, N., "Clostridium difficile: The Emerging Epidemic", Mayo Clinic Proceedings, Nov. 2012, vol. 87, No. 11, 1037-1039.
Sandora, T.J., et al., "Epidemiology and risk factors for Clostridium difficile infection in children", Pediatr Infect Dis J, Jul. 2011; 30(7):580-4.
Saulnier, Delphine et al, Gut Microbiome News, Gastrointestinal microbiome signatures of pediatric patients with irritable bowel syndrome, 2001.
Savini, M. et al, Cryopreservation Studies, Pilot-scale Production and Viability Analysis of Freeze-Dried Probiotic Bacteria Using Different Protective Agents, 2010.
Schloissnig, S. et al, Microbiome papers, Geniomic variation landscape of the human gut microbiome, 2013.
Schloissnig, S. et al, Microbiome papers, Genomic variation landscape of the human gut microbiome, 2013.
Schwan, Anna et al, C Diff Treatment with Fecal Transplant, Relapsing clostridium difficile enterocolitis cure by rectal infusion of normal feces, 1984.
Schwartz, K., et al., "Severe clinical outcome is uncommon in Clostridium difficile infection in children: aretrospective cohort study", BMC Pediatr, Jan. 31, 2014; 14:28 (6 pgs.).
See, I., et al., "NAP1 Strain Type Predicts Outcome From Clostridium difficile Infection", Clin Infect Dis, May 2014; 58 (10):1394-400.
Segata, N. et al, Microbiome papers, Composition of the adult digestive tract bacterial microbiome based on seven mouth surfaces, tonsils, throat and stool samples, 2012.
Senior, K., "Faecal transplantation for recurrent C difficile diarrhoea", Lancet Infect Dis., Mar. 2013; 13(3):200-1.
Sghir et al., "Quantification of Bacterial Groups within Human Fecal Flora by Oligonucleotide Probe Hybridization," Applied and Environmental Microbiology, vol. 66, No. 5, p. 2263-2266 (May 2000).
Sha, S., et al., "Systematic review: faecal microbiota transplantation therapy for digestive and nondigestive disorders in adults and children", Aliment Pharmacol Ther, May 2014; 39(10):1003-32.
Shamekhi, F. et al, Drug Delivery, Cell viability of microencapsulated Bifidobacterium animalis subsp. lactis under freeze-drying, storage and gastrointestinal tract simulation conditions, 2013.
Shaughnessy, M.K., et al., "Unnecessary Antimicrobial Use in Patients With Current or Recent Clostridium difficile Infection", Infect Control Hosp Epidemiol 2013;34(2):109-116.
Shim, J., GI Disease—General, Gut microbiola in inflammatory bowel disease, 2013.
Shwartz, Margot et al, C-Diff Treatment with Fecal Transplant, Norovirus Gastroenteritis After Fecal Microbiota Transplantation for Treatment of Colostridium Difficile Infection Despite Asymptonatic Donors and Lack of Sick Contacts, 2013.
Silverman, Michael et al, C Diff Treatment with Fecal Transplant, Success of self-administered home fecaltransplantation for chronic clostridium difficile infection, 2010.
Simoes, C. et al, Analysis of Species in Feces, Habitual Dietary Intake Is Associated with Stool Microbiotacomposition in Monozygotic Twins, 2013.
Simon, M.S., "Cost-Effectiveness of Fidaxomicin for Clostridium difficile Treatment", Clinical Infectious Diseases, 2014; 58(4):603.
Smith, M.B., et al., "Policy: How to regulate faecal transplants", Nature, Feb. 20, 2014; 506(7488):290-1.
Sobhani, I. et al, GI Disease—General, Microbial dysbiosis and colon carcinogenesis: could colon cancer be considered a bacteria-related disease?, 2013.
Sofi, A., et al., "Physician outlook toward fecal microbiota transplantation in the treatment of Clostridium difficile infection", Am J Gastroenterol, Oct. 2013; 108(10):1661-2.
Sokol, H et al, Analysis of Species in Feces, Low counts of Faecalibacterium prausnitzii in colitis microbiota, 2009.
Solari, P., et al., "Tempered enthusiasm for Fecal transplantation", Clin Infect Dis, Apr. 23, 2014 (3 pgs.).
Song, Y. et al, FMT Studies and Reviews, Microbiota dynamics in patients treated with fecal microbiotatransplantation for recurrent clostridium difficile infection, 2013.
Sough, E., et al., "Systematic Review of Intestinal Microbiota Transplantation (Fecal Bacteriotherapy) for Recurrent Clostridium difficile Infection", (2011 ), 994-1002.
Stahlmann, J., et al., "Detection of nosocomial Clostridium difficile infections with toxigenic strains despite negative toxin A/B testing on stool samples", Clin Microbiol Infect, Jan. 23, 2014 (10 pgs.).
Stephen, Alison et al, Analysis of Species in Feces, The microbial contribution to human fecal mass, 1980.
Stern, A. et al, Microbiome papers, CRISPR targeting reveals a reservoir of common phages associated with the human gut microbiome, 2012.
Stock, J., "Gut microbiota: an environmental risk factor for cardiovascular disease", Atherosclerosis, Aug. 2013; 229 (2):440-2.
Sunkesula, V.C., et al., "Does empirical Clostridium difficile infection {CDI} therapy result in false-negative CDI diagnostic test results?", Clin Infect Dis, Aug. 2013; 57(4):494-500.
Surawicz, C. et al, Industry, Guidelines for diagnosis, treatment and prevention of clostridium difficile infections, 2013.
Suvarna, K., et al., "Case Studies of Microbial Contamination in Biologic Product Manufacturing", Microbiology, Jan./ Feb. 2011, pp. 50-57.
Swift, Homer, Bacterial Presentation via Freezing, Preservation of stock cultures of bacteria by freezing and drying, 1921.
Tang, P., et al, "Limited clinical utility of Clostridium difficile toxin testing in infants in a pediatric hospital", Diagn Microbiol Infect Dis, Jun. 2005; 52(2):91-4.
Tannock, Gerald, Microbiome papers, The bowel microbiota and inflammatory bowel diseases, 2010.
Taori, S.K., et al., "A prospective study of community-associated Clostridium difficile infections: The role of antibiotics and co-infections", J Infect, Apr. 26, 2014 (11 pgs.).
Taur, Y., et al., "Harnessing microbiota to kill a pathogen: Fixing the microbiota to treat Clostridium difficile infections" Nat Med., Mar. 2014; 20(3):246-7.
Taur, Y., et al., "Intestinal domination and the risk of bacteremia in patients undergoing allogeneic hematopoietic stem cell transplantation", Clin Infect Dis., Oct. 2012; 55(7):905-14.
Teather, Ronald, Bacterial Presentation via Freezing, Maintenance of Laboratory Strains of Obligaetly Anaerobic Rumen Bacteria, 1982.
Tedeschi, Rosamaria; De Paoli, Paolo, Bacterial Preservation via Freezing, Collection and Preservation ofMicroorganisms, 2011.
Tickler, I.A., et al., "Strain Types and Antimicrobial Resistance Patterns of Clostridium difficile Isolates from the United States: 2011-2013", Antimicrob Agents Chemother, Apr. 21, 2014 (17 pgs.).
Tjellstrom, B. et al, Pediatrics, Effect of exclusive enteral nutrition on gut microflora function in children with Chron's disease, 2012.
Topac (<http://topac.com/bag.html>, Accessed Sep. 27, 2016 (Mar. 26, 2012)).
Tottey, W. et al, Microbiome papers, The Human Gut Chip "HuGChip", an Explorative Phylogenetic Microarray for Determining Gut Microbiome Diversity at Family Level, 2013.
Tran, M.C., et al., "Therapy of Clostridium difficile infection: perspectives on a changing paradigm", Expert Opin Pharmacother., Dec. 2013; 14(17):2375-86.
Trnka et al., "Well-plate freeze-drying: a high throughput platform for screening of physical properties of freeze-dried formulations,"

(56) References Cited

OTHER PUBLICATIONS

Journal Pharmaceutical Development and Technology, vol. 20, 2015—Issue 1, 65-73, (Published online Jan. 2013).
Tsai, S. et al, Drug Delivery, Hyaluronan-cisplatin conjugate nanoparticles embedded in Eudragit S100-coated pectin/alginate microbeads for colon drug delivery, 2013.
Tshudin-Sutter, S., et al., "Clostridium difficile: novel insights on an incessantly challenging disease", Curr Opin Infect Dis., Aug. 2012; 25(4):405-11.
Tuomola et al., "Quality assurance criteria for probiotic bacteria," Am J Clin Nutr., 73(suppl) pp. 393S-8S (2001).
Tvede, M et al, C Diff Treatment with Fecal Transplant, Bacteriotherapy for chronic relapsing clostridium difficile diarrhea in six patients, 1989.
Tyler, A., et al., "Analyzing the Human Microbiome: A 'How To' guide for Physicians", Am J Gastroenterol, Apr. 22, 2014 (11 pgs.).
Udayappan, S.D., et al., "Intestinal microbiota and fecal transplantation as treatment modality for insulin resistance and type 2 diabetes mellitus", Clin Exp Immunol., Feb. 15, 2014 (17 pgs.).
Vaarala, O., "Human intestinal microbiota and type 1 diabetes", Curr Diab Rep., Oct. 2013.; 13(5):601-7.
Vaishnavi, C., "Fecal microbiota transplantation for management of Clostridium difficile infection", Indian JGastroenterol, Apr. 20, 2014 (7 pgs.).
Van den Abbeele, P. et al., Microbiome papers, Prebiotics, fecal transplants and microbial network units to stimulate biodiversity of the human gut microbiome, 2013.
Van der Meulen, R et al., Cryopreservation Studies, In vitro kinetic analysis of oligofructos consumption bybacteroides and bifidobacterium spp indicates different degredation mechanisms, 2006.
Van der Wilden, G., et al., "Fulminant Clostridium difficile colitis: Prospective development of a risk scoring system", J Trauam Actue Care Surg., vol. 76, No. 2, 2014, 424-30.
Van Nood, E. et al, C Diff Treatment with Fecal Transplant, Duodenal infusion of donor feces for recurrentcolostridium difficile, 2013.
Van Nood, E. et al, FMT Studies and Reviews, Fecal microbiota transplantation: facts and controversies, 2014.
Van Nood, E., et al., "Struggling with Recurrent Clostridium difficile Infections: Is Donor Faeces the Solution?", EuroSurveill. 2009;14(34), pp. 1-6.
Vandenplas, Y., et al., "Fecal Microbial Transplantation in a One-Year-Old Girl with Early Onset Colitis—Caution Advised", J Pediatr Gastroenterol Nutr., Jan. 2, 2014 (11 pgs.).
VanNood, E et al, C Diff Treatment with Fecal Transplant, Struggling with recurrent clostridium difficile infections: is donor faeces the solution?, 2009.
Varela, E. et al, Ulcerative Colitis, Colonisation by Faecalibacterium prausnilzii and maintenance of clinical remission in patients with ulcerative colitis, 2013.
Varkonyi, I., et al., "Findings of a hospital surveillance-based outcome evaluation study for Clostridium difficile—Associated colitis", Clin Microbiol. Infect., Apr. 28, 2014 (18 pgs.).
Vartoukian, S., et al., "Strategies for culture of 'unculturable' bacteria", FEMS Microbiol Lett 309 (2010) 1-7.
Varum, F.J.O. et al., Drug Delivery, A novel coating concept for ileo-colonic drug targeting: Proof of concept in humans using scintigraphy, 2013.
Viaud, S. et al, Microbiome papers, Supplementary materials for: The intestinal microbiota modulates the anticancer immuni effects of cyclophosphamide, 2013.
Viaud, S. et al, Microbiome papers, The intestinal microbiota modulates the anticancer immuni effects of cyclophosphamide, 2013.
Vigsnaes, L. et al, Ulcerative Colitis, Microbiotas from UC patients display altered metabolism and reduced ability of LAB to colonize mucus, 2012.
Vincent, C., et al., "Reductions in intestinal Clostridiales precede the development of nosocomial Clostridium difficile infection", Microbiome, 2013, 1:18 (11 pgs.).

Viswanathan, VK, Microbiome papers, The meddling microbes midst our medicines, 2013.
Vrieze, A. et al, FMT Studies and Reviews, Fecal transplant: A safe and sustainable clinical therapy for restoring intestinal microbial balance in human disease?, 2013.
Vrieze, A. et al., FMT Studies and Reviews, Transfer of Intestinal Microbiota From Lean Donors Increases Insulin Sensitivity in Individuals With Metabolic Syndrome, 2012.
Vujkovic-Cvijin, I. et al, Microbiome papers, Dysbiosis of the Gut Microbiota Is Associated with HIV Disease Progression and Tryptophan Catabolism2013.
Vyas, D et al, C Diff Treatment with Fecal Transplant, Stool therapy may become a preferred treatment of recurrent Colostridium difficile, 2013.
Wang, W., et al., "Low Vitamin D Level Is an Independent Predictor of Poor Outcomes in Clostridium difficile -- Associated Diarrhea", Ther Adv Gastroenterol., 2014; 7(1):14-19.
Wasfy et al. "Comparison of Preservation Media for Storage of Stool Samples," Journal of Clinical Microbiology, vol. 33, No. 8, pp. 2176-2178 (Aug. 1995).
Wasfy, M. et al, Microbial Preservation, Comparison of preservation media for storage of stool samples, 1995.
Weingarden, A. et al, FMT Studies and Reviews, Microbiota transplantation restores normal fecal bile acid composition in recurrent clostridium difficile infection, 2013.
Wendt, J_ M., et al., "Clostridium difficile Infection Among Children Across Diverse US Geographic Locations", Pediatrics, vol. 133, No. 4, Apr. 2014 (10 pgs.).
Wenfeng, S. et al, Cryopreservation Studies, Appraising freeze-drying for storage of bacteria and their ready access in a rapid toxicity assessment assay, 2013.
Wesemann, D. et al, Pediatrics, Microbial colonization influences early B-lineage development in the gut lamina propria, 2013.
Wettstein et al., "Fecal Bacteriotherapy—An Effective Treatment for Relapsing Symtomatic Clostridium Difficile Infection," United European Gastroenterology Federation—UEGF, Poster Presentation Wednesday Oct. 31, 2007.
Wiegand, P.N., et al., "Clinical and economic burden of Clostridium difficile infection in Europe: a systematic review Jf healthcare-facility-acquired infection", Journal of Hospital Infection 81 (2012) 1-14.
Wu, G. et al, Microbiome papers, Linking long-term dietary patterns with gut microbial enterotypes, 2011.
Wu, G.; Lewis, J., Microbiome papers, Analysis of the Human Gut Microbiome and Association With Disease, 2013.
Wu, N. et al, Cancer, Dysbiosis Signature of Fecal Microbiota in Colorectal Cancer Patients, 2013.
Wu, T. et al, Analysis of Species in Feces, Gut microbiota dysbiosis and bacterial community assembly associated with cholesterol gallstones in large-scale study, 2013.
Xu, Q. et al, Drug Delivery, KGM and PMAA based pH-sensitive interpenetrating polymer network hydrogel for controlled drug release, 2013.
Yoon et al., "Treatment of Refractory/Recurrent C. difficile-associated Disease by Donated Stool Transplanted Via Colonoscopy—A Case Series of 12 Patients," J Clin Gastroenterol 44:562-566 (2010).
Yoshimoto, S. et al., Obesity Related, Obesity-induced gut microbial metabolite promotes liver cancer through senescence secretome, 2013.
Young, Vincent, Microbiome papers, The Intestinal Microbiota in Health and Disease, 2012.
Youngster, I., et al., "Fecal Microbiota Transplant for Relapsing Clostridium difficile Infection Using a Frozen noculum From Unrelated Donors: A Randomized, Open-Label, Controlled Pilot Study", Clin Infect Dis., Apr. 2014;58 11): 1515-22.
Youngster, I., et al., "Supplementary Appendix: Fecal Microbiota Transplant for Relapsing Clostridium difficile infection Using a Frozen Inoculum From Unrelated Donors: A Randomized, Open-Label, Controlled Pilot Study", Clin Infect Dis., Apr. 2014 (6 pgs.).
Zainah, H.; Silverman, A., Ulcerative Colitis, Fecal Bacteriotherapy: A Case Report in an immunosuppressed Patient with Ulcerative Colitis and Recurrent Clostridium difficile Infection, 2012.

(56) References Cited

OTHER PUBLICATIONS

Zhang, F. et al, Chrohn's disease, Fecal microbiota transplantation for severe enterocolonic fistulizing Crohn's disease, 2013.

Zhao et al., "Effect of protective agents, freezing temperature, rehydration media on viability of malolactic bacteria subjected to freeze-drying," Journal of Applied Microbiology vol. 99, pp. 333-338 (2005).

Zhao, G et al, Bacterial Presentation via Freezing, Effect of protective agents, freezing temperature, rehydration media on viability of malolactic bacteria subjected to freeze-drying, 2005.

Zhao, L. et al, Microbiome papers, Targeting the human genome—microbiome axis for drug discovery: inspirations fom global systems biology and traditional chinese medicine, 2013.

Zilberberg, M.D., et al., "Development and Validation of a Recurrent Clostridium difficile Risk-Prediction Model", Journal of Hospital Medicine, Apr. 4, 2014 (6 pgs.).

Zilberberg, M.D., et al., "Clostridium difficile Infections among Hospitalized Children, United States, 1997-2006", Emerging Infectious Diseases, vol. 16, No. 4, Apr. 2010, 604-609.

Zimmer, C., "Bacterial Ecosystems Divide People Into 3 Groups, Scientists Say", The New York Times, Apr. 20, 2011 (4 pgs.).

Zoetendal, erwin et al, Analysis of Species in Feces, Mucosa-Associated bacteria in the human gastrointestinal tract are uniformly distributed along the colon and differ from the community recovered from feces, 2002.

Alexander Khoruts et al. "Understanding the mechanisms of faecal microbiota transplantation" Nat Rev Gastroenterol Hepatol. Sep. 2016; 13(9); pp. 508-516.

Examination Report dated Aug. 16, 2023 received in Chinese Patent Application No. 202111357079.X.

Examination Report received in European Patent Application No. 18170305.9 dated Sep. 11, 2023.

Minirin Nasal Spray. Desmopressin [online]. Consumer Medicine Information, May 2001 [retrieved on Sep. 15, 2008]. Retrieved from the Internet: <URL:http://medsafe.govt.nz/Consumers/CMI/m/MinirinNSpray.htm>.

Non-Final Office Action received in U.S. Appl. No. 18/062,934, dated Sep. 19, 2023.

Non-Final Office Action received in U.S. Appl. No. 18/128,890, dated Oct. 13, 2023.

Office Action dated Aug. 17, 2023, received in Chinese Patent Application No. 201980053918.3.

Office Action dated May 3, 2023, received in European Patent Application No. 19734627.3.

Chen ((2004) DNA-based vaccines against cancer. University of Southampton, Doctoral Thesis). (Year: 2004).

Cleland et al. "Glycine betaine as a cryoprotectant for prokaryotes" J. Microbiol. Meth., 58:31-38 (2004) (Abstract).

Coyne et al., "Niche-Specific Features of the Intestinal Bacterioidales" J. Bacterial., 190(2):736-742 (2008).

FDA, 21 C.F.R & 211.1 et seq (accessed Dec. 14, 2015).

Ley et al. "Worlds within worlds: evolution of the vertebrate gut microbiota". Nat Rev Microbiol. Oct. 2008; 6(10): 776-788.

Non-Final Office Action received in U.S. Appl. No. 17/260,126 dated Dec. 20, 2023.

Non-Final Office Action received in U.S. Appl. No. 18/136,213 dated Nov. 16, 2023.

Nsabimana et al., App. Env. Microbiol., 69(7):3826-3832 (2003).

Office Action received in U.S. Appl. No. 18/136,213 dated Nov. 22, 2023.

Shu et al., J. Clin. Microbiol., 50(11 ):3575-3580 (2012).

Smith, T. "Fecal transplants to cure Clostridium difficile infection—Aetiology". http://scienceblogs.com/aetiology/2007 /12/1 7 /fecal-transplants-to-cu re-clos/. Published on Dec. 17, 2007.

Tuomola et al.,Am. J. Clin. Nutr., 73(suppl):393S-398S (2001).

Turnbaugh et al. The effect of diet on the human gut microbiome: a metagenomic analysis in humanized gnotobiotic mice. Sci Transl Med. Nov. 11, 2009 ;1 (6).

WHO, Technical Report Series, No. 908 (2003).

WRMS(<http://www.marinespecies.org/aphia.php?p=taxdetails&id=393070> Accessed May 16, 2018).

* cited by examiner

BACTERIOTHERAPY FOR CLOSTRIDIUM DIFFICILE COLITIS

CROSS-REFERENCE TO RELATED APPLICATIONS

This application is a continuation of U.S. application Ser. No. 15/964,228, filed Apr. 27, 2018, which is a continuation of U.S. application Ser. No. 15/251,725, filed Aug. 30, 2016, which is a continuation of U.S. application Ser. No. 14/093, 913, filed Dec. 2, 2013, now U.S. Pat. No. 9,463,208, which is a continuation of U.S. application Ser. No. 13/576,573, filed on Oct. 17, 2012, now U.S. Pat. No. 9,629,881, which is a 371 national stage of PCT/US2011/000184, filed on Feb. 1, 2011, which claims the benefit of priority under 35 U.S.C. § 119 to U.S. Application No. 61/337,283, filed on Feb. 1, 2010, and which also claims priority to U.S. Application No. 61/351,184, filed on Jun. 3, 2010, all of which applications are herein incorporated by reference.

BACKGROUND

Between 300 and 1000 different species of bacteria reside in a healthy gastrointestinal (GI) tract. Clostridia are anaerobic, spore-forming bacteria. Certain species of *Clostridium* are pathogens, producing toxins that can be harmful to humans. *Clostridium difficile* ("C. diff") is one species of *Clostridium* that, if overpopulated in the GI tract, can release toxins that can cause a number of symptoms, including bloating, constipation, diarrhea, inflammation, abdominal pain, among others that, in certain cases, can lead to death.

When stressed, *Clostridium difficile* create spores that can tolerate extreme conditions many active bacteria cannot. Generally, clostridia do not compete well in a healthy GI tract. However, antibiotics can disrupt the normal intestinal flora, leading to an overgrowth of *Clostridium difficile*. In certain examples, the *Clostridium difficile* spores can be resistant to various antibiotics. Thus, as the normal intestinal flora is cleared, the *Clostridium difficile* spores remain, leading to a large population of *Clostridium difficile*.

Overview

This document discusses, among other things, receiving a plurality of donor fecal samples from a plurality of donors and storing and indexing each respective donor fecal samples using at least one characteristic of the respective donor fecal sample. In an example, the donor fecal sample can be screened and processed for subsequent use in fecal bacteriotherapy to displace pathogenic or undesired organisms in the digestive track of a patient with healthy or desirable gut micriobiota.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
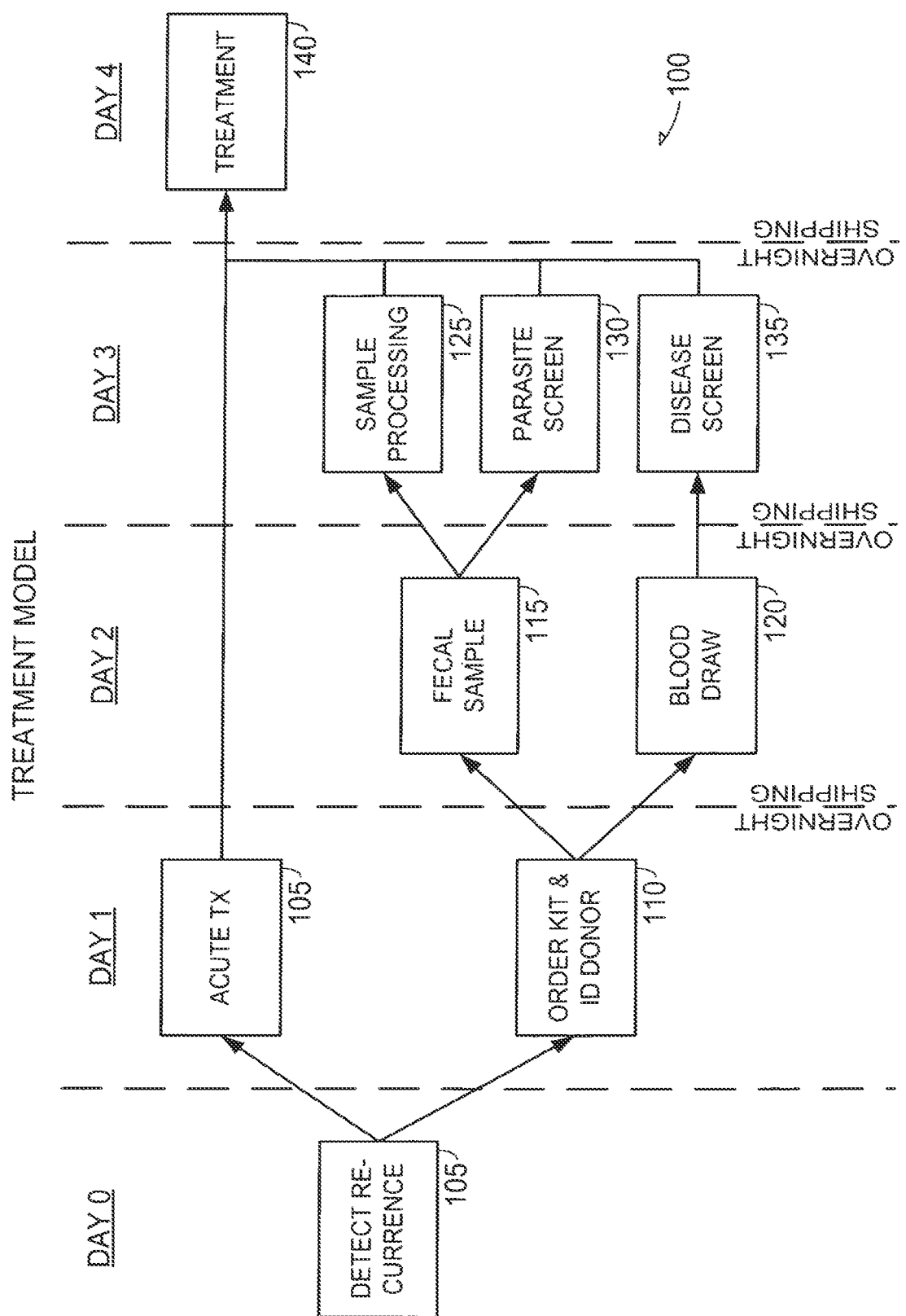
FIG. 1 illustrates generally an example of a Treatment Model including a 5 day fecal bacteriotherapy treatment cycle.

Each individual has a personalized gut microbiota including an estimated 500 to 5000 or more species of bacteria, fungi, archaea and other microorganisms, up to 100 trillion individual organisms, that reside in the digestive tract, providing a host of useful symbiotic functions, including aiding in digestion, providing nutrition for the colon, producing vitamins, stimulating the immune system, assisting in defense against exogenous bacteria, modulating energy metabolism, etc. However, an improperly balanced or functioning gut microbiota may play a role in certain diseases or afflictions, such as pseudomembranous colitis, *Clostridium difficile* colitis, antiobiotic-associated diarrhea (AAD), ulcerative colitis (UC), pouchitis, irritable bowel syndrome (IBS), obesity, among others.

Accordingly, the present inventor has recognized, among other things, systems and methods for providing bacteriotherapy to treat afflictions associated with the gut microbiota, including *Clostridium difficile* colitis, by displacing pathogenic organisms in the digestive track of a patient with healthy bacterial flora, or bacterial flora intended to benefit a specific individual with an affliction associated with the gut microbiota. In an example, the systems and methods described herein can provide a convenient, hygienic mechanism, capable of meshing with existing capabilities and routines of existing clinics and hospitals, for providing bacteriotherapy to a patient. In certain examples, similar treatment can be effective for patients with other diseases, such as IBS, crones, ulcer, or other gastrointestinal or digestive tract related disease. In other examples, bacteriotherapy can be used to aid in weight loss, displacing ineffective flora in the gut with a more effective microbiota.

For example, estimates of *Clostridium difficile* overpopulation incidence vary from 1.5 to 2.7 million occurrences in the United States per year, and are growing. In one estimate, hospital discharges with *Clostridium difficile* doubled from 2001 to 2005, with an estimated 5% to 25% compound annual growth rate. Current estimates indicate that patients affected by *Clostridium difficile* overpopulation experience increased hospital stays from 3 to 36 days, with nearly 20% of affected patients being readmitted within 180 days, each more likely to be discharged to long-term care facilities than patients not affected. The financial impact of *Clostridium difficile* is estimated at $1 to $3 billion annually. Moreover, an estimated 300 patient deaths per day are attributable to *Clostridium difficile* overpopulation, a mortality rate of 1 to 7.7%, and increasing.

Traditional treatment for *Clostridium difficile* typically includes application antibiotics. Metronidazole ("Flagyl®") is the antibiotic of choice due to low price and high efficacy. However, for recurring cases (up to 20% of total cases, for example, resistant to metronidazole), pregnant patients, or patients younger than 10 years of age, vancomycin ("Vancocin®") is typically used. However, vancomycin, although typically having fewer side effects than metronidazole, has a much higher cost and may lead to resistance of existing *Clostridium difficile* to further antibiotics.

At first occurrence, antibiotic treatment for *Clostridium difficile* can be acutely effective to treat diarrhea within 2 to 4 days at a rate approximately at or above 90%. However, *Clostridium difficile* typically recurs after the first occurrence (e.g., several days to 12 weeks after cessation of antibiotics) at an estimated 20% rate (e.g., 15%-30%). However, for each recurrence following the first recurrence, the rate increases greatly, to an estimated 40% rate following the second recurrence, and to greater than an estimated 60% rate or greater thereafter. It is estimated that approximately 5% of patients have 6 or more recurrences.

Treatment for *Clostridium difficile* typically varies after each occurrence. For example, for first mild to moderate recurrence, metronidazole can be administered orally (e.g., at a dose of 500 mg, three times daily ("TID") for 10 to 14 days). For a second recurrence, vancomycin can be administered orally in tapered or pulsed doses (e.g., at a dose of 125 mg, four times daily ("QID") for 14 days; at a dose of 125 mg, twice daily ("BID") for 7 days; at a dose of 125 mg, once daily ("QD") for 7 days; at a dose of 125 mg, once every 2 days for 8 days (four doses); at a dose of 125 mg, once every 3 days for 15 days (five doses), etc.). For a third recurrence, vancomycin can be applied at greater doses (e.g., at a dose of 125 mg, four times daily ("QID") for 14 days), combined with any of the other options for recurrent infection, such as intravenous immunoglobulin (e.g., at a dose of 400 mg per kg body weight, once every three weeks, for a total of two or three doses depending on effect), or rifamycin following the vancomycin doses (e.g., the rifamycin at a dose of 400 mg, twice daily ("BID") for 14 days), etc.

In an example, bacteriotherapy to treat *Clostridium difficile* or one or more other diseases or afflictions of the digestive tract can be provided using a combination of antibiotics and re-population of a healthy or desired bacterial flora. In certain examples, the re-population of bacterial flora can include fecal bacteriotherapy, or fecal transplant.

The process of fecal bacteriotherapy can include introducing a fecal sample of a healthy donor, or a donor having one or more desired characteristics, into a gastrointestinal tract of a patient to repopulate a healthy or desirable gut micriobiota. In certain examples, prior to introduction of the fecal sample, the patient's intestinal flora can be disrupted using antibiotics, such that the healthy or desirable gut microbiota, once introduced into the patient, can easily populate the gastrointestinal tract.

In an example, a kit of parts can be created to aid in fecal transplant. In an example, a donation kit can be shipped to a clinician. The donation kit can include equipment for blood and fecal samples from the patient or, in certain examples, a healthy donor. Because much of the patient's gut micriobiota is anaerobic, many organisms can die with exposure to air. In an example, the donation kit can include materials to ship the blood and fecal samples without harming the samples (e.g., quick freeze, dry ice, etc.).

Once shipped to a facility (e.g., one location, regional locations, many locations, etc.), the samples can be tested, and *Clostridium difficile* or the presence or absence of one or more other diseases or conditions can be confirmed. In other examples, a healthy fecal sample can be tested and prepared for use as a treatment.

In an example, once the patient's samples are tested to verify the disease or condition, or the donor's samples are tested to verify health or other compatibility (e.g., the existence of one or more desired condition, etc.), a treatment can be prepared (e.g., using the healthy donor fecal sample, at least a portion of one or more healthy stored fecal samples, such as material from a fecal bank, etc.) and shipped back to the clinician for delivery to and treatment of the patient. In certain examples, the treatment is preserved (e.g., frozen, etc.) during shipping. The kit can include the processed fecal sample or treatment in a sterile container, such as a nasogastric (NG) tube, a vial (e.g., for use with a retention enema), a gastro-resistant capsule (e.g., acid-bio resistant to reach the intestinal tract, having a sterile outside), etc. In an example, once received, the clinician can store the contents in a manner to preserve the micriobiota until ready to be inserted into the patient.

FIG. 1 illustrates generally an example of a Treatment Model 100 including a 5 day fecal bacteriotherapy treatment cycle. At 105, day 0, recurrence of a condition, such as *Clostridium difficile* colitis or one or more other afflictions associated with the gut microbiota, is detected in a patient. In an example, the condition can be detected using the presentation of one or more symptoms associated with the condition, such as diarrhea during or following hospitalization, etc. In other examples, at 105, the occurrence of one or more undesirable conditions, such as obesity, etc., can be detected, triggering application of the Treatment Model 100.

At 105, day 1, acute treatment ("TX") can be prescribed for or administered to the patient. In an example, the acute treatment can include administration of vancomycin (e.g., at a dose of 125 mg) four times daily for 4 days (QID.times.4 d). In other examples, other doses can be used. However, the dosage can be less than traditional antibiotic treatment due to the subsequent repopulation of healthy or desired gut micriobiota from the fecal bacteriotherapy to combat conditions or pathogens that would otherwise remain in the gastrointestinal tract (e.g., *Clostridium difficile* spores, etc.).

At 110, day 1, a bacteriotherapy kit can be ordered, and in certain examples, a donor can be identified. In an example, the bacteriotherapy kit can be directed for use with a specific donor and recipient. In many examples, for patients or intended recipients having an improperly balanced or functioning gut microbiota, it can be desirable to identify a donor having a healthy gut microbiota similar to the patient's healthy gut microbiota. Accordingly, a donor having a similar diet from a similar or close geographic region, typically a spouse or close relative, provides the best probability of quickly returning the patient's healthy gut microbiota. However, in other examples, other desired donor characteristics can be selected, such as a physical characteristic, etc. In an example, the bacteriotherapy kit can be overnight shipped to a clinician at a treatment facility, such as a hospital or clinic, or otherwise quickly delivered to or stocked by the clinician or at the treatment facility. In certain examples, the kit can include a cooling mechanism, such as dry ice or one or more other cooling mechanisms, configured to preserve subsequent biological samples during transport.

At 115, day 2, the fecal sample can be taken from a proposed donor, from the patient, or from both the proposed donor and the patient. At 120, day 2, a blood sample can be taken from the proposed donor, from the patient, or from both the proposed donor and the patient. In an example, the fecal sample and the blood draw can be stored in a bag (e.g., a fecal sample bag or a blood bag, respectively) or one or more other storage mediums, such as a test tube or one or more other storage containers. In certain examples, to preserve the samples for testing and subsequent use, at least one of the fecal sample or the blood draw can be cooled, such as by using dry ice, etc. In an example, the fecal sample and the blood draw can be overnight shipped or otherwise quickly delivered to a facility for testing and processing the donor fecal sample.

At 125, day 3, the fecal sample can be processed for use in fecal bacteriotherapy. In an example, the processing can include at least one of blending or filtering the fecal sample and preparing the sample for delivery to the patient, such as by nasogastric (NG) tube, retention enema, colonoscopy delivery, or an oral tablet or capsule, resistant to stomach acid (e.g., using an enteric coating, etc.), configured to reach the gastrointestinal tract. Accordingly, the processing can include placement into a sterile delivery container, such as a bag configured for use with an NG tube or retention enema. At 130, day 3, the fecal sample can be screened for parasites or other pathogens, prior to or after processing. At 135, day 3, the blood draw can be screened for communicable disease, to further ensure a healthy donor fecal sample.

In an example, following screening and processing, the processed sample can be cooled and overnight shipped to the clinician or caregiver at the treatment facility. At 140, day 4, following the last dose of acute treatment (e.g., using antibiotics), fecal bacteriotherapy can be provided to the patient using the donor's processed fecal sample.

Figure 2:
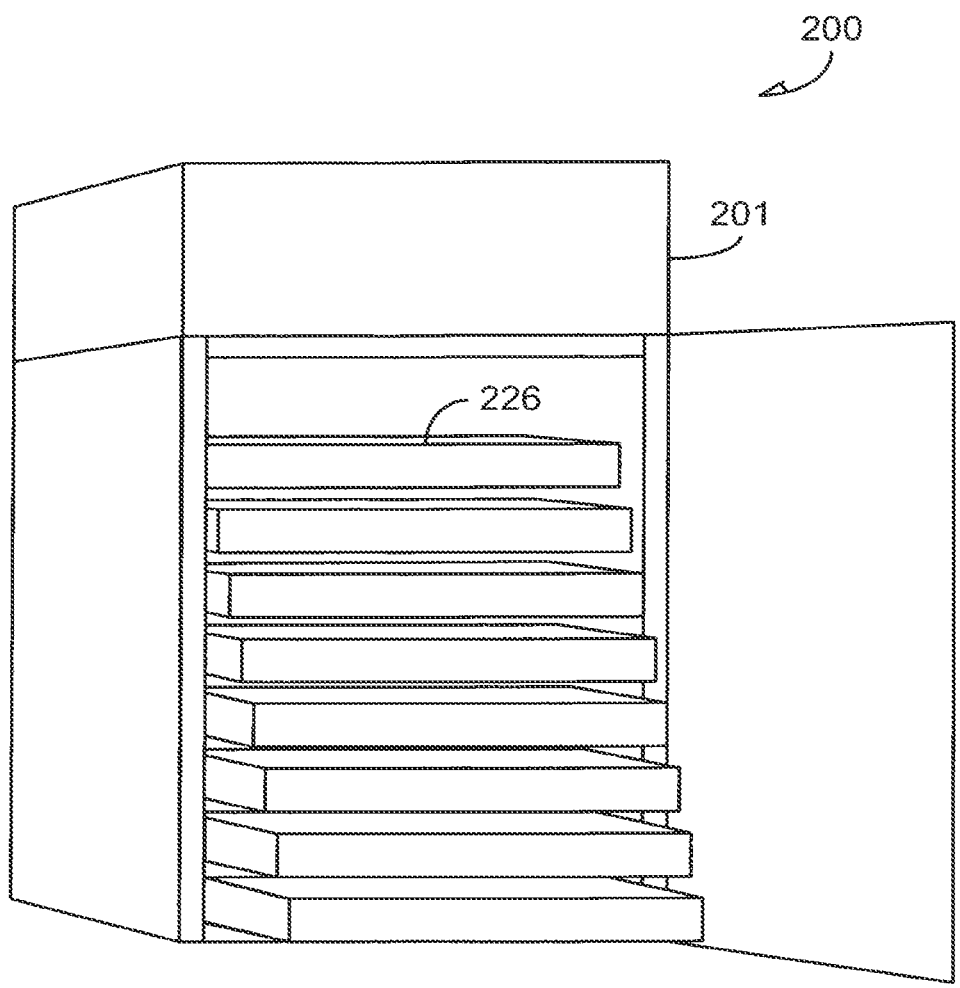
FIG. 2 illustrates generally an example of a bacteriotherapy bank configured to store one or more processed and screened donor fecal samples.

FIG. 2 illustrates generally an example of a bacteriotherapy bank 200 including a cooling device (e.g., a refrigerator 201, etc.) having a plurality of shelves (e.g., such as a first shelf 226, etc.) configured to store one or more processed and screened donor fecal samples. In an example, the bacteriotherapy bank 200 can be configured to provide healthy donor fecal samples to a single patient or a plurality of patients using at least a portion of a fecal sample from a single healthy donor, or using at least a portion of a fecal sample from a plurality of healthy donors. The fecal bank allows for treatment of a first number of patients with a smaller number of donors, reducing the cost of testing and screening the donors and testing, screening, and processing the donor fecal samples.

In an example, the bacteriotherapy bank 200 can be supplied using a pool of anonymous, pre-screened donors, and can stock a number of frozen, screened aliquots (single donor) for subsequent use. In an example, a healthy donor can prepare fecal and blood samples, unattached to a specific patient. In an example, the donor fecal samples can be indexed using various donor information, or using one or more characteristic of the donor fecal sample, such as a geographic location of the donor, the source of the donor's diet, the type of the donor's diet, the donor's ethnicity, body type, age, sex, health status, or medical history, or other information of the donor or the donor's fecal sample. In an example, people in the same geographic location, or having similar diets, can have similar gut microbiota. It can be desirable to match the gut microbiota of the healthy donor to the patient (e.g., similar reasons to using a healthy family member for a donor). In an example, the donor samples can be indexed using a computer indexing system configured to store the various donor information or one or more characteristic, can be indexed using a label on a bag or shelf in the bacteriotherapy bank 200, or can be indexed using one or more other indexing operations.

In an example, using the bacteriotherapy bank 200, exposure and risk associated with the procedure can be limited by using a donor for only a specified number of samples (e.g., to prevent the accidental exposure of patients to infected donor material). In other examples, it can be advantageous for an obese patient to receive the gut microbiota of a healthy or thin donor, or of a donor having a desired body composition or type, as the healthy or thin donors gut flora may aid in weight management or management of one or more other characteristic, such as weight gain, etc.

In certain examples, the bacteriotherapy bank 200 can store material at temperatures of −20 degrees Celsius, the materials including donor fecal samples, processed fecal samples, fecal samples in delivery form, such as in an NG tube, vial, oral pill, etc., or one or more other material.

Figure 3:
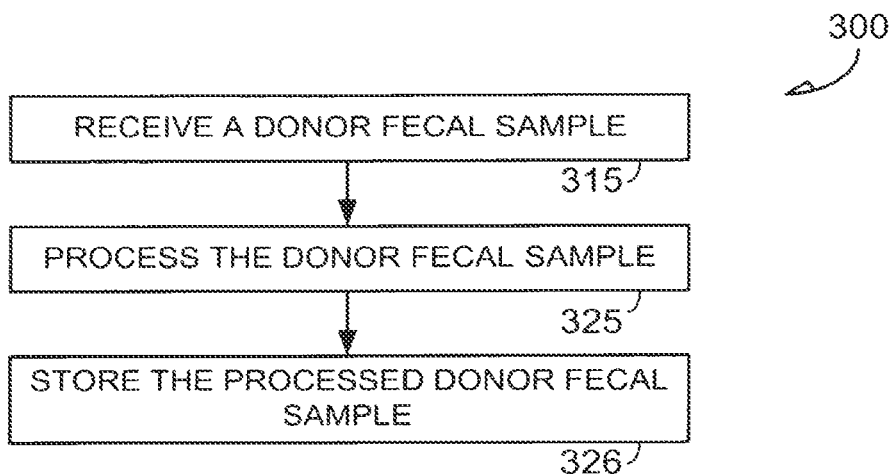
FIG. 3 illustrates generally an example of a method of receiving and storing donor fecal samples.

FIG. 3 illustrates generally an example of a method 300 of receiving and storing donor fecal samples. At 315, a donor fecal sample is received. At 325, the donor fecal sample can be processed and prepared for use in fecal bacteriotherapy, including, in certain examples, testing or screening the donor fecal sample for one or more diseases or conditions, or placing the processed donor fecal sample in deliverable form. At 326, the processed donor fecal sample can be stored prior to use, such as using a cooling mechanism such as dry ice, a refrigerator, or one or more other mechanisms.

Figure 4:
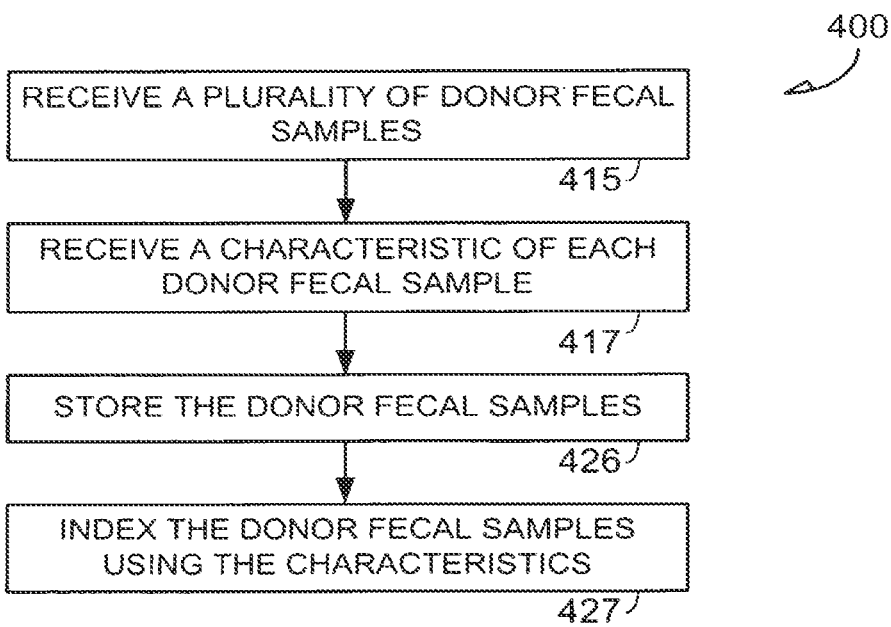
FIG. 4 illustrates generally an example of a method of receiving, storing, and indexing donor fecal samples.

FIG. 4 illustrates generally an example of a method 400 of receiving, storing, and indexing donor fecal samples. At 415, a plurality of donor fecal samples are received. At 417, at least one characteristic of each donor fecal sample, or at least one characteristic of each donor of each donor fecal sample, is received. At 426, the donor fecal sample can be stored prior to use, such as using a cooling mechanism such as dry ice, a refrigerator, or one or more other mechanisms. At 427, the donor fecal samples can be indexed using the at least one characteristic. In certain examples, the donor fecal samples can be selected for use with a patient using one or more shared or desired characteristic.

In other examples, fecal bacteriotherapy (e.g., using the bacteriotherapy bank or kit models described above) can be used to treat or affect one or more other diseases or conditions. For example, inflammatory bowel disease (IBD) (e.g., including Crohn's disease, ulcerative colitis (UC), pouchitis, etc.) affects more than one million people in the United States alone. Irritable bowel syndrome accounts for nearly one-third of all gastrointestinal office visits, affecting more than 36 million patients, with few tools or treatments available to provide effective treatment. In certain examples, patients afflicted with IBD or IBS could benefit from a different gut microbiota providing different functions to the gastrointestinal tract.

Further, fecal bacteriotherapy can be used to treat obesity. Because the gut micriobiota in obese individuals is different from non-obese individuals, and because gut micriobiota influences energy metabolism, displacing the gut micriobiota of an obese individual with the guy micriobiota of a non-obese individual.

Additional Notes & Examples

In Example 1, a method can optionally include receiving a plurality of donor fecal samples from a plurality of donors, receiving a characteristic of each of the plurality of donor fecal samples, storing at least a portion of each of the plurality of donor fecal samples, and indexing each of the plurality of donor fecal samples using a characteristic of the respective donor fecal sample.

In Example 2, a characteristic of the donor fecal sample of Example 1 can optionally include a characteristic of the fecal biota of the donor fecal sample.

In Example 3, the characteristic of the donor fecal sample of any one or more of Examples 1-2 can optionally include at least one of a physical characteristic or a dietary characteristic of the donor.

In Example 4, the physical characteristic of the donor of any one or more of Examples 1-3 can optionally include at least one of a medical condition of the donor, a donor body mass index (BMI), a donor weight, a combination of a donor height and the donor weight, or a donor body fat percentage.

In Example 5, the physical characteristic of the donor of any one or more of Examples 1-4 can optionally include a medical condition of the donor, and the characteristic of the donor fecal sample can optionally include the presence or absence of a medical condition of the donor.

In Example 6, the medical condition of the donor of any one or more of Examples 1-5 can optionally include at least one of a metabolic disorder or a digestive disorder.

In Example 7, the metabolic disorder of any one or more of Examples 1-6 can optionally include diabetes mellitus, and the digestive disorder of any one or more of Examples 1-6 can optionally include a gastrointestinal (GI) disorder including at least one of irritable bowel syndrome (IBS) or inflammatory bowel disease (IBD).

In Example 8, the dietary characteristic of the donor of any one or more of Examples 1-7 can optionally include at least one of a donor geographic consumption region, a donor diet, or a donor religion.

In Example 9, the receiving the plurality of donor fecal samples of any one or more of Examples 1-8 can optionally include processing each of the plurality of donor fecal samples, including homogenizing and filtering each of the donor fecal samples.

In Example 10, the receiving the plurality of donor fecal samples of any one or more of Examples 1-9 can optionally include receiving a plurality of donor fecal samples from a plurality of screened donors.

In Example 11, any one or more of Examples 1-10 can optionally include receiving a request for donor fecal matter, and selecting a fecal dose using information from the request and the indexed characteristics of the plurality of donor fecal samples, wherein the fecal dose optionally includes at least a portion of at least one of the stored donor fecal samples and is configured to be provided to a patient.

In Example 12, any one or more of Examples 1-11 can optionally include providing the fecal dose to the patient to transfer a functioning biota in the patient.

In Example 13, the providing the fecal dose to the patient to transfer the functioning biota in the patient of any one or more of Examples 1-12 can optionally include to treat at least one of antibiotic associated diarrhea or a *Clostridium difficile* infection.

In Example 14, the receiving the request for donor fecal matter of any one or more of Examples 1-13 can optionally include receiving at least one desired characteristic.

In Example 15, the receiving the at least one desired characteristic of any one or more of Examples 1-14 can optionally include receiving at least one of a desired physical characteristic or a desired dietary characteristic of the donor.

In Example 16, the storing at least a portion of each of the plurality of donor fecal samples of any one or more of Examples 1-15 can optionally include storing at least a portion of each of the plurality of donor fecal samples in a patient-deliverable form.

In Example 17, the storing at least a portion of each of the plurality of donor fecal samples in the patient-deliverable form of any one or more of Examples 1-16 can optionally include storing at least a portion of each of the plurality of donor fecal samples in at least one of an ingestible capsule configured to be delivered to an intestinal tract of a patient through the mouth of the patient, an ampule configured for use in an antegrade gastrointestinal (GI) delivery approach to the intestinal tract of the patient, or an ampule configured for use in a retrograde GI delivery approach to the intestinal tract of the patient.

In Example 18, the receiving the plurality of donor fecal samples of any one or more of Examples 1-17 can optionally include receiving wet fecal samples and processing each of the received donor fecal samples, wherein the processing each of the received donor fecal samples of any one or more of Examples 1-17 can optionally include homogenizing, filtering, and adding a cryoprotectant to each of the donor fecal samples, and wherein the storing at least a portion of each of the plurality of donor fecal samples in a patient-deliverable form of any one or more of Examples 1-17 can optionally include freezing each of the plurality of donor fecal samples in the patient-deliverable form to maintain viability of the biota of the donor fecal samples.

In Example 19, any one or more of Examples 1-18 can optionally include preparing a plurality of fecal doses using one or more donor fecal samples from a single donor, wherein the plurality of fecal doses are configured to be provided to a plurality of patients.

In Example 20, any one or more of Examples 1-19 can optionally include preparing a fecal dose configured to be provided to a single patient using a plurality of donor fecal samples.

In Example 21, the preparing the fecal dose of any one or more of Examples 1-20 can optionally include combining at least a portion of a first donor fecal sample and a second donor fecal sample, wherein the first and second donor samples have at least one different characteristic.

In Example 22, a fecal bank can optionally include a plurality of fecal storage containers configured to store each of a plurality of donor fecal sample and an indexing system, configured to associate, for each of the plurality of donor fecal samples, a characteristic of the donor fecal sample with the respective donor fecal sample.

In Example 23, the characteristic of the donor fecal sample of any one or more of Examples 1-22 can optionally include at least one of a physical characteristic or a dietary characteristic of the donor.

In Example 24, the characteristic of the donor fecal sample of any one or more of Examples 1-23 can optionally include a characteristic of the fecal biota of the donor fecal sample.

In Example 25, the physical characteristic of the donor of any one or more of Examples 1-24 can optionally include at least one of a medical condition of the donor, a donor body mass index (BMI), a donor weight, a combination of a donor height and the donor weight, or a donor body fat percentage.

In Example 26, the physical characteristic of the donor of any one or more of Examples 1-25 can optionally include a medical condition of the donor and wherein the characteristic of the donor fecal sample includes the presence or absence of a medical condition of the donor.

In Example 27, the medical condition of the donor of any one or more of Examples 1-26 can optionally include at least one of a metabolic disorder or a digestive disorder, wherein the metabolic disorder includes diabetes mellitus, and wherein the digestive disorder includes a gastrointestinal (GI) disorder including at least one of irritable bowel syndrome (IBS) or inflammatory bowel disease (IBD).

In Example 28, the dietary characteristic of the donor of any one or more of Examples 1-27 can optionally include at least one of a donor geographic consumption region, a donor diet, or a donor religion.

In Example 29, the plurality of donor fecal samples of any one or more of Examples 1-28 can optionally include wet fecal samples and wherein the plurality of fecal storage containers are configured to store frozen, wet donor fecal samples to maintain viability of the biota of the donor fecal samples.

In Example 30, the plurality of fecal storage containers of any one or more of Examples 1-29 can optionally include a plurality of patient-deliverable fecal storage containers.

In Example 31, the plurality of patient-deliverable fecal storage containers of any one or more of Examples 1-30 can optionally include at least one of an ingestible capsule configured to be delivered to an intestinal tract of a patient through the mouth of the patient, an ampule configured for use in an antegrade gastrointestinal (GI) delivery approach to the intestinal tract of the patient, or an ampule configured for use in a retrograde GI delivery approach to the intestinal tract of the patient.

In Example 32, a system can include, or can optionally be combined with any portion or combination of any portions of any one or more of Examples 1-31 to include, subject matter that can include means for performing any one or more of the functions of Examples 1-31, or a machine-readable medium including instructions that, when performed by a machine, cause the machine to perform any one or more of the functions of Examples 1-31.

In Example 33, a method optionally includes receiving a donor fecal sample from a donor, processing the donor fecal sample, wherein the processing includes homogenizing the donor fecal sample, and storing at least a portion of the processed donor fecal sample.

In Example 34, the receiving the donor fecal sample from the donor of any one or more of Examples 1-33 can optionally include receiving a plurality of donor fecal samples from a plurality of donors, wherein the processing the donor fecal sample of any one or more of Examples 1-33 can optionally include processing each of the plurality of donor fecal samples, wherein the processing of any one or more of Examples 1-33 can optionally include homogenizing each of the donor fecal samples, and wherein the storing at least a portion of the processed donor fecal sample of any one or more of Examples 1-33 can optionally include storing at least a portion of each of the plurality of processed donor fecal samples.

In Example 35, any one or more of Examples 1-34 optionally includes receiving a characteristic of each of the plurality of donor fecal samples, and indexing each of the plurality of donor fecal samples using a characteristic of the respective donor fecal sample.

In Example 36, the characteristic of the donor fecal sample of any one or more of Examples 1-35 can optionally include a characteristic of the fecal biota of the donor fecal sample.

In Example 37, the characteristic of the donor fecal sample of any one or more of Examples 1-36 can optionally include at least one of a physical characteristic or a dietary characteristic of the donor.

In Example 38, the physical characteristic of the donor of any one or more of Examples 1-37 can optionally include at least one of a medical condition of the donor, a donor body mass index (BMI), a donor weight, a combination of a donor height and the donor weight, or a donor body fat percentage.

In Example 39, the physical characteristic of the donor of any one or more of Examples 1-38 can optionally include a medical condition of the donor, and wherein the characteristic of the donor fecal sample of any one or more of Examples 1-38 can optionally include the presence or absence of a medical condition of the donor.

In Example 40, the medical condition of the donor of any one or more of Examples 1-39 can optionally include at least one of a metabolic disorder or a digestive disorder, wherein the metabolic disorder of any one or more of Examples 1-39 can optionally include diabetes mellitus, and wherein the digestive disorder includes a gastrointestinal (GI) disorder of any one or more of Examples 1-39 can optionally include at least one of irritable bowel syndrome (IBS) or inflammatory bowel disease (IBD).

In Example 41, the dietary characteristic of the donor of any one or more of Examples 1-40 can optionally include at least one of a donor geographic consumption region, a donor diet, or a donor religion.

In Example 42, any one or more of Examples 1-41 can optionally include receiving a request for donor fecal matter, and selecting a fecal dose using information from the request and the indexed characteristics of the plurality of donor fecal samples, wherein the fecal dose of any one or more of Examples 1-41 can optionally include at least a portion of at least one of the stored donor fecal samples and is configured to be provided to a patient.

In Example 43, any one or more of Examples 1-42 can optionally include providing the fecal dose to the patient to transfer a functioning biota in the patient.

In Example 44, the providing the fecal dose to the patient to transfer the functioning biota in the patient of any one or more of Examples 1-43 can optionally include to treat at least one of antibiotic associated diarrhea or a *Clostridium difficile* infection.

In Example 45, the receiving the request for donor fecal matter of any one or more of Examples 1-44 can optionally include receiving at least one desired characteristic.

In Example 46, the receiving the at least one desired characteristic of any one or more of Examples 1-45 can optionally include receiving at least one of a desired physical characteristic or a desired dietary characteristic of the donor.

In Example 47, any one or more of Examples 1-46 can optionally include preparing a fecal dose configured to be provided to a single patient using a plurality of processed donor fecal samples.

In Example 48, the preparing the fecal dose of any one or more of Examples 1-47 can optionally include combining at least a portion of a first donor fecal sample and a second donor fecal sample, wherein the first and second donor samples have at least one different characteristic.

In Example 49, the processing the donor fecal sample of any one or more of Examples 1-48 can optionally include filtering the donor fecal sample.

In Example 50, the receiving the donor fecal sample of any one or more of Examples 1-49 can optionally include receiving a donor fecal sample from a screened donor.

In Example 51, the storing at least a portion of the processed donor fecal sample of any one or more of Examples 1-50 can optionally include storing at least a portion of the processed donor fecal sample in a patient-deliverable form.

In Example 52, the storing at least a portion of the processed donor fecal sample in the patient-deliverable form of any one or more of Examples 1-51 can optionally include storing at least a portion of each of the plurality of donor fecal samples in at least one of an ingestible capsule configured to be delivered to an intestinal tract of a patient through the mouth of the patient, an ampule configured for use in an antegrade gastrointestinal (GI) delivery approach to the intestinal tract of the patient, or an ampule configured for use in a retrograde GI delivery approach to the intestinal tract of the patient.

In Example 53, the receiving the donor fecal sample of any one or more of Examples 1-52 can optionally include receiving a wet fecal sample, wherein the processing the donor fecal sample of any one or more of Examples 1-52 can optionally include adding a cryoprotectant to the donor fecal sample, and wherein the storing at least a portion of the processed donor fecal sample in the patient-deliverable form of any one or more of Examples 1-52 can optionally include freezing at least a portion of the processed donor fecal sample in the patient-deliverable form to maintain viability of the biota of the donor fecal sample.

In Example 54, the adding the cryoprotectant of any one or more of Examples 1-53 can optionally include at least one of glycol, glycerol, dimethyl sulfoxide (DMSO), dairy milk, or soy milk.

In Example 55, any one or more of Examples 1-54 can optionally include preparing a plurality of fecal doses using one or more processed donor fecal samples from a single donor, wherein the plurality of fecal doses are configured to be provided to a plurality of patients.

In Example 56, at least a portion of the stored donor fecal sample of any one or more of Examples 1-55 can optionally be configured to be provided to an intestinal tract of a patient that is not the donor to a condition of the patient.

In Example 57, the condition of any one or more of Examples 1-56 can optionally include at least one of a disease or an infection of or in the patient.

In Example 58, the condition of any one or more of Examples 1-57 can optionally include at least one of antibiotic associated diarrhea of the patient or a *Clostridium difficile* infection in the patient.

In Example 59, a system can include, or can optionally be combined with any portion or combination of any portions of any one or more of Examples 1-58 to include, subject matter that can include means for performing any one or more of the functions of Examples 1-58, or a machine-readable medium including instructions that, when performed by a machine, cause the machine to perform any one or more of the functions of Examples 1-58.

In Example 60, a method can optionally include receiving a donor fecal sample from a donor, and storing at least a portion of the donor fecal sample in a patient-deliverable form.

In Example 61, the receiving the donor fecal sample of any one or more of Examples 1-60 can optionally include receiving a plurality of donor fecal samples from a plurality of donors, and wherein the storing at least a portion of the donor fecal sample in the patient-deliverable from of any one or more of Examples 1-60 can optionally include storing at least a portion of each of the plurality of processed donor fecal samples in a patient-deliverable form.

In Example 62, any one or more of Examples 1-61 can optionally include receiving a characteristic of each of the plurality of donor fecal samples, and indexing each of the plurality of donor fecal samples using a characteristic of the respective donor fecal sample.

In Example 63, the characteristic of the donor fecal sample of any one or more of Examples 1-62 can optionally include a characteristic of the fecal biota of the donor fecal sample.

In Example 64, the characteristic of the donor fecal sample of any one or more of Examples 1-63 can optionally include at least one of a physical characteristic or a dietary characteristic of the donor.

In Example 65, the physical characteristic of the donor of any one or more of Examples 1-64 can optionally include at least one of a medical condition of the donor, a donor body mass index (BMI), a donor weight, a combination of a donor height and the donor weight, or a donor body fat percentage.

In Example 66, the physical characteristic of the donor of any one or more of Examples 1-65 can optionally include a medical condition of the donor and wherein the characteristic of the donor fecal sample of any one or more of Examples 1-65 can optionally include the presence or absence of a medical condition of the donor.

In Example 67, the medical condition of the donor of any one or more of Examples 1-66 can optionally include at least one of a metabolic disorder or a digestive disorder, wherein the metabolic disorder of any one or more of Examples 1-66 can optionally include diabetes mellitus, and wherein the digestive disorder of any one or more of Examples 1-66 can optionally include a gastrointestinal (GI) disorder including at least one of irritable bowel syndrome (IBS) or inflammatory bowel disease (IBD).

In Example 68, the dietary characteristic of the donor of any one or more of Examples 1-67 can optionally include at least one of a donor geographic consumption region, a donor diet, or a donor religion.

In Example 69, any one or more of Examples 1-68 can optionally include receiving a request for donor fecal matter and selecting a fecal dose using information from the request and the indexed characteristics of the plurality of donor fecal samples, wherein the fecal dose includes at least a portion of at least one of the stored donor fecal samples and is configured to be provided to a patient.

In Example 70, any one or more of Examples 1-69 can optionally include providing the fecal dose to the patient to transfer a functioning biota in the patient.

In Example 71, the providing the fecal dose to the patient to transfer the functioning biota in the patient of any one or more of Examples 1-70 can optionally include to treat at least one of antibiotic associated diarrhea or a *Clostridium difficile* infection.

In Example 72, the receiving the request for donor fecal matter of any one or more of Examples 1-71 can optionally include receiving at least one desired characteristic.

In Example 73, the receiving the at least one desired characteristic of any one or more of Examples 1-72 can optionally include receiving at least one of a desired physical characteristic or a desired dietary characteristic of the donor.

In Example 74, any one or more of Examples 1-73 can optionally include preparing a fecal dose configured to be provided to a single patient using a plurality of processed donor fecal samples.

In Example 75, the preparing the fecal dose of any one or more of Examples 1-74 can optionally include combining at least a portion of a first donor fecal sample and a second donor fecal sample, wherein the first and second donor samples have at least one different characteristic.

In Example 76, the receiving the donor fecal sample of any one or more of Examples 1-75 can optionally include receiving a donor fecal sample from a screened donor.

In Example 77, any one or more of Examples 1-76 can optionally include processing the received donor fecal sample, wherein the processing includes homogenizing the donor fecal sample, wherein the storing at least a portion of the donor fecal sample in the patient-deliverable form of any one or more of Examples 1-76 can optionally include storing at least a portion of the processed donor fecal sample.

In Example 78, the processing the donor fecal sample of any one or more of Examples 1-77 can optionally include filtering the donor fecal sample.

In Example 79, the receiving the donor fecal sample of any one or more of Examples 1-78 can optionally include receiving a wet fecal sample, wherein the processing the donor fecal sample of any one or more of Examples 1-78 can optionally include adding a cryoprotectant to the donor fecal sample, and wherein the storing at least a portion of the processed donor fecal sample in the patient-deliverable form of any one or more of Examples 1-78 can optionally include freezing at least a portion of the processed donor fecal sample in the patient-deliverable form to maintain viability of the biota of the donor fecal sample.

In Example 80, any one or more of Examples 1-79 can optionally include preparing a plurality of fecal doses using one or more processed donor fecal samples from a single donor, wherein the plurality of fecal doses are configured to be provided to a plurality of patients.

In Example 81, the storing at least a portion of the donor fecal sample in the patient-deliverable form of any one or more of Examples 1-80 can optionally include storing at least a portion of the donor fecal sample in at least one of an ingestible capsule configured to be delivered to an intestinal tract of a patient through the mouth of the patient, an ampule configured for use in an antegrade gastrointestinal (GI) delivery approach to the intestinal tract of the patient, or an ampule configured for use in a retrograde GI delivery approach to the intestinal tract of the patient.

In Example 82, the storing at least a portion of the donor fecal sample in the ingestible capsule of any one or more of Examples 1-81 can optionally include storing at least a portion of the donor fecal sample in a gastro-resistant capsule.

In Example 83, any one or more of Examples 1-82 can optionally include a patient-deliverable fecal storage container configured to store at least a portion of a processed donor fecal sample configured to be provided to an intestinal tract of a patient that is not the donor to treat a condition of the patient.

In Example 84, of any one or more of Examples 1-83 can optionally include a plurality of patient-deliverable fecal storage containers configured to store at least a portion of each of a plurality of processed donor fecal samples, and an indexing system, configured to associate, for each of the plurality of processed donor fecal samples, a characteristic of the processed donor fecal sample with the respective processed donor fecal sample.

In Example 85, the characteristic of the donor fecal sample of any one or more of Examples 1-84 can optionally include a characteristic of the fecal biota of the donor fecal sample.

In Example 86, the characteristic of the donor fecal sample of any one or more of Examples 1-85 can optionally include at least one of a physical characteristic or a dietary characteristic of the donor.

In Example 87, the physical characteristic of the donor of any one or more of Examples 1-86 can optionally include at least one of a medical condition of the donor, a donor body mass index (BMI), a donor weight, a combination of a donor height and the donor weight, or a donor body fat percentage.

In Example 88, the physical characteristic of the donor of any one or more of Examples 1-87 can optionally include a medical condition of the donor, wherein the characteristic of the donor fecal sample of any one or more of Examples 1-87 can optionally include the presence or absence of a medical condition of the donor.

In Example 89, the medical condition of the donor of any one or more of Examples 1-88 can optionally include at least one of a metabolic disorder or a digestive disorder, wherein the metabolic disorder of any one or more of Examples 1-88 can optionally include diabetes mellitus, and wherein the digestive disorder of any one or more of Examples 1-88 can optionally include a gastrointestinal (GI) disorder including at least one of irritable bowel syndrome (IBS) or inflammatory bowel disease (IBD).

In Example 90, the dietary characteristic of the donor of any one or more of Examples 1-89 can optionally include at least one of a donor geographic consumption region, a donor diet, or a donor religion.

In Example 91, the processed donor fecal sample of any one or more of Examples 1-90 can optionally include a wet fecal sample, and wherein the patient-deliverable fecal storage container of any one or more of Examples 1-90 can optionally be configured to store at least a portion of a frozen, wet donor fecal sample to maintain viability of the biota of the donor fecal sample.

In Example 92, the patient-deliverable fecal storage container of any one or more of Examples 1-91 can optionally include at least one of an ingestible capsule configured to be delivered to an intestinal tract of a patient through the mouth of the patient, an ampule configured for use in an antegrade gastrointestinal (GI) delivery approach to the intestinal tract of the patient, or an ampule configured for use in a retrograde GI delivery approach to the intestinal tract of the patient.

In Example 93, the condition of the patient of any one or more of Examples 1-92 can optionally include at least one of a disease or an infection of or in the patient.

In Example 94, the condition of the patient of any one or more of Examples 1-93 can optionally include at least one of antibiotic associated diarrhea of the patient or a *Clostridium difficile* infection in the patient.

In Example 95, a system can include, or can optionally be combined with any portion or combination of any portions of any one or more of Examples 1-94 to include, subject matter that can include means for performing any one or more of the functions of Examples 1-94, or a machine-readable medium including instructions that, when performed by a machine, cause the machine to perform any one or more of the functions of Examples 1-94.

In Example 96, a method can optionally include selecting a fecal dose for treatment of a condition of a patient, wherein the fecal dose includes at least a portion of a donor fecal sample from a donor and is configured to be provided to an intestinal tract of the patient, wherein the patient is not the donor, and wherein the selecting the fecal dose includes using a characteristic of the donor.

In Example 97, the condition of the patient of any one or more of Examples 1-96 can optionally include a patient weight above a desired target weight.

In Example 98, the condition of the patient of any one or more of Examples 1-97 can optionally include obesity.

In Example 99, the characteristic of the donor fecal sample of any one or more of Examples 1-98 can optionally include a characteristic of the fecal biota of the donor fecal sample.

In Example 100, the characteristic of the donor of any one or more of Examples 1-99 can optionally include at least one of a physical characteristic or a dietary characteristic of the donor.

In Example 101, the physical characteristic of the donor of any one or more of Examples 1-100 can optionally include at least one of a donor body mass index (BMI), a donor weight, a combination of a donor height and the donor weight, or a donor body fat percentage.

In Example 102, the physical characteristic of the donor of any one or more of Examples 1-101 can optionally include a medical condition of the donor, and wherein the characteristic of the donor fecal sample of any one or more of Examples 1-101 can optionally include the presence or absence of a medical condition of the donor.

In Example 103, the dietary characteristic of the donor of any one or more of Examples 1-102 can optionally include at least one of a donor geographic consumption region, a donor diet, or a donor religion.

In Example 104, any one or more of Examples 1-103 can optionally include providing information about the dietary characteristic of the donor to the patient, wherein the dietary characteristic includes a donor diet.

In Example 105, the characteristic of the donor of any one or more of Examples 1-104 can optionally include the physical characteristic of the donor and the dietary characteristic of the donor.

In Example 106, the fecal dose of any one or more of Examples 1-105 can optionally include at least a portion of a plurality of donor fecal samples from a plurality of donors, and wherein the selecting the fecal dose of any one or more of Examples 1-105 can optionally include using at least one characteristic of the plurality of donors.

In Example 107, any one or more of Examples 1-106 can optionally include receiving the donor fecal sample from the donor, processing the donor fecal sample, wherein the processing of any one or more of Examples 1-106 can optionally include homogenizing the donor fecal sample, and wherein the fecal dose of any one or more of Examples 1-106 can optionally include at least a portion of the processed donor fecal sample.

In Example 108, the receiving the donor fecal sample from the donor of any one or more of Examples 1-107 can optionally include receiving a plurality of donor fecal samples from a plurality of donors, wherein the processing the donor fecal sample of any one or more of Examples 1-107 can optionally include processing each of the plurality of donor fecal samples, wherein the processing of any one or more of Examples 1-107 can optionally include homogenizing each of the donor fecal samples, and storing at least a portion of each of the plurality of processed donor fecal samples.

In Example 109, any one or more of Examples 1-108 can optionally include receiving a characteristic of each of the plurality of donor fecal samples, and indexing each of the plurality of donor fecal samples using a characteristic of the respective donor fecal sample.

In Example 110, the fecal dose of any one or more of Examples 1-109 can optionally include at least a portion of at least one of the stored processed donor fecal samples and is configured to be provided to a patient In Example 111, the receiving the donor fecal sample of any one or more of Examples 1-110 can optionally include receiving a wet fecal sample, wherein the processing the donor fecal sample includes adding a cryoprotectant to the donor fecal sample, storing at least a portion of the processed donor fecal sample in a patient-deliverable form, and wherein the storing at least a portion of the processed donor fecal sample in the patient-deliverable form of any one or more of Examples 1-110 can optionally include freezing at least a portion of the processed donor fecal sample in the patient-deliverable form to maintain viability of the biota of the donor fecal sample.

In Example 112, any one or more of Examples 1-111 can optionally include receiving the donor fecal sample from the donor, storing at least a portion of the donor fecal sample in a patient-deliverable form, and wherein the selecting the fecal dose of any one or more of Examples 1-111 can optionally include selecting at least one stored donor fecal sample.

In Example 113, the storing at least a portion of the donor fecal sample in the patient-deliverable form of any one or more of Examples 1-112 can optionally include storing at least a portion of the donor fecal sample in at least one of an ingestible capsule configured to be delivered to an intestinal tract of a patient through the mouth of the patient, an ampule configured for use in an antegrade gastrointestinal (GI) delivery approach to the intestinal tract of the patient, or an ampule configured for use in a retrograde GI delivery approach to the intestinal tract of the patient.

In Example 114, the condition of any one or more of Examples 1-113 can optionally include at least one of a disease or an infection of or in the patient.

In Example 115, the condition of any one or more of Examples 1-116 can optionally include at least one of antibiotic associated diarrhea of the patient or a *Clostridium difficile* infection in the patient.

In Example 116, any one or more of Examples 1-115 can optionally include preparing a plurality of fecal doses using one or more donor fecal samples from a single donor, wherein the plurality of fecal doses are configured to be provided to a plurality of patients In Example 117, any one or more of Examples 1-116 can optionally include receiving a plurality of donor fecal samples from a plurality of donors, receiving a characteristic of each of the plurality of donors, storing at least a portion of each of the plurality of donor fecal samples, indexing each of the plurality of donor fecal samples using at least one characteristic of the respective donors, receiving a request for donor fecal matter, and selecting a fecal dose for treatment of a condition of a patient in response to the received request for donor fecal matter, wherein the fecal dose of any one or more of Examples 1-116 can optionally include at least a portion of a stored donor fecal sample and is configured to be provided to an intestinal tract of the patient, wherein the patient is not the donor, wherein the condition of the patient of any one or more of Examples 1-116 can optionally include a patient weight above a desired patient weight, and wherein the selecting the fecal dose includes using a physical characteristic of the donor of the fecal dose and a dietary characteristic of the donor of the fecal dose.

In Example 118, the physical characteristic of the donor of any one or more of Examples 1-117 can optionally include at least one of a donor body mass index (BMI), a donor weight, a combination of a donor height and the donor weight, or a donor body fat percentage.

In Example 119, the dietary characteristic of the donor of any one or more of Examples 1-118 can optionally include at least one of a donor geographic consumption region, a donor diet, or a donor religion.

In Example 120, any one or more of Examples 1-119 can optionally include providing information about the dietary characteristic of the donor to the patient, wherein the dietary characteristic includes a donor diet.

In Example 121, the fecal dose of any one or more of Examples 1-120 can optionally include at least a portion of a plurality of donor fecal samples from a plurality of donors, and wherein the selecting the fecal dose of any one or more of Examples 1-120 can optionally include using a physical characteristic of the plurality of donors of the fecal dose and a dietary characteristic of the plurality of donors of the fecal dose.

In Example 122, a system can include, or can optionally be combined with any portion or combination of any portions of any one or more of Examples 1-121 to include, subject matter that can include means for performing any one or more of the functions of Examples 1-121, or a machine-readable medium including instructions that, when performed by a machine, cause the machine to perform any one or more of the functions of Examples 1-121.

In Example 123, a method can optionally include providing a kit to a clinician, the kit enabling the clinician to store and transport a donor fecal sample from a donor to a central facility, receiving the frozen donor fecal sample from the clinician at the central facility, screening the donor fecal sample for at least one of a parasite, a pathogen, a disease, or an unhealthy condition of the donor, and providing a fecal dose to the clinician to be administered to a patient, wherein the fecal dose includes at least a portion of at least one donor fecal sample.

In Example 124, any one or more of Examples 1-123 can optionally include, receiving a characteristic of the donor fecal sample, storing at least a portion the donor fecal sample, and indexing the donor fecal sample using the characteristic of the donor fecal sample.

In Example 125, the characteristic of the donor fecal sample of any one or more of Examples 1-124 can optionally include a characteristic of the fecal biota of the donor fecal sample.

In Example 126, the characteristic of the donor fecal sample of any one or more of Examples 1-125 can optionally include at least one of a physical characteristic or a dietary characteristic of the donor.

In Example 127, the physical characteristic of the donor of any one or more of Examples 1-126 can optionally include at least one of a medical condition of the donor, a donor body mass index (BMI), a donor weight, a combination of a donor height and the donor weight, or a donor body fat percentage.

In Example 128, the physical characteristic of the donor of any one or more of Examples 1-127 can optionally include a medical condition of the donor, and wherein the characteristic of the donor fecal sample of any one or more of Examples 1-127 can optionally include the presence or absence of a medical condition of the donor.

In Example 129, the medical condition of the donor of any one or more of Examples 1-128 can optionally include at least one of a metabolic disorder or a digestive disorder.

In Example 130, the metabolic disorder of any one or more of Examples 1-129 can optionally include diabetes mellitus, and wherein the digestive disorder of any one or more of Examples 1-129 can optionally include a gastrointestinal (GI) disorder including at least one of irritable bowel syndrome (IBS) or inflammatory bowel disease (IBD).

In Example 131, the dietary characteristic of the donor of any one or more of Examples 1-130 can optionally include at least one of a donor geographic consumption region, a donor diet, or a donor religion.

In Example 132, the providing the kit to the clinician of any one or more of Examples 1-131 can optionally include providing a plurality of kits to one or more clinicians, wherein the receiving the frozen donor fecal sample from the clinician of any one or more of Examples 1-131 can optionally include receiving a plurality of frozen donor fecal samples from one or more clinicians, wherein the screening the donor fecal sample of any one or more of Examples 1-131 can optionally include screening a plurality of donor fecal samples, wherein the receiving the characteristic of the donor fecal sample of any one or more of Examples 1-131 can optionally include receiving a characteristic of each of the plurality of donor fecal samples, wherein the storing at least a portion of the donor fecal sample of any one or more of Examples 1-131 can optionally include storing at least a portion of the plurality of donor fecal samples, and wherein the indexing the donor fecal sample of any one or more of Examples 1-131 can optionally include indexing each the plurality of donor fecal samples using a characteristic of the respective donor fecal sample.

In Example 133, any one or more of Examples 1-132 can optionally include receiving a request for donor fecal matter, and selecting the fecal dose to be provided to the patient from a plurality of stored fecal doses using information from the request and the indexed characteristics of the plurality of donor fecal samples.

In Example 134, the receiving the request for donor fecal matter of any one or more of Examples 1-133 can optionally include receiving at least one desired characteristic.

In Example 135, the receiving the at least one desired characteristic of any one or more of Examples 1-136 can optionally include receiving at least one of a desired physical characteristic or a desired dietary characteristic of the donor.

In Example 136, the storing at least a portion the donor fecal sample of any one or more of Examples 1-135 can optionally include storing at least a portion of the donor fecal sample in a patient-deliverable form.

In Example 137, the storing at least a portion of the donor fecal sample in a patient-deliverable form of any one or more of Examples 1-136 can optionally include storing at least a portion of each of the plurality of donor fecal samples in at least one of an ingestible capsule configured to be delivered to an intestinal tract of a patient through the mouth of the patient, an ampule configured for use in an antegrade gastrointestinal (GI) delivery approach to the intestinal tract of the patient, or an ampule configured for use in a retrograde GI delivery approach to the intestinal tract of the patient.

In Example 138, any one or more of Examples 1-137 can optionally include processing the donor fecal sample, the processing the donor fecal sample of any one or more of Examples 1-137 can optionally include homogenizing and filtering the donor fecal sample.

In Example 139, the processing the donor fecal sample of any one or more of Examples 1-138 can optionally include adding a cryoprotectant to the donor fecal sample, and wherein the storing at least a portion of the donor fecal sample of any one or more of Examples 1-138 can optionally include freezing the donor fecal sample to maintain viability of the biota of the donor fecal sample.

In Example 140, any one or more of Examples 1-139 can optionally include providing the fecal dose to the patient to transfer a functioning biota in the patient.

In Example 141, the providing the fecal dose to the patient to transfer the functioning biota in the patient of any one or more of Examples 1-140 can optionally include to treat at least one of antibiotic associated diarrhea or a *Clostridium difficile* infection.

In Example 142, any one or more of Examples 1-141 can optionally include providing a kit to the clinician, the kit enabling the clinician to store and transport a donor blood sample from the donor to the central facility, receiving the frozen donor blood sample from the clinician at the central facility, and screening the donor blood sample for at least one of a parasite, a pathogen, a disease, or an unhealthy condition of the donor.

In Example 143, the providing the kit to the clinician of any one or more of Examples 1-142 can optionally include providing a kit enabling the clinician to store and transport a wet fecal sample from the patient to the central facility.

In Example 144, the providing the kit to the clinician of any one or more of Examples 1-143 can optionally include providing a kit enabling the clinician to store, freeze, and transport the wet fecal sample from the patient to the central facility.

In Example 145, a system can include, or can optionally be combined with any portion or combination of any portions of any one or more of Examples 1-144 to include, subject matter that can include means for performing any one or more of the functions of Examples 1-144, or a machine-readable medium including instructions that, when performed by a machine, cause the machine to perform any one or more of the functions of Examples 1-144.

In Example 146, a method can optionally include providing a kit to a clinician, the kit enabling the clinician to store and transport a patient fecal sample from a patient to a central facility, receiving the frozen patient fecal sample from the clinician at the central facility, and providing a fecal dose to the clinician to be administered to the patient, wherein the fecal dose of any one or more of Examples 1-145 can optionally include at least a portion of at least one donor fecal sample.

In Example 147, any one or more of Examples 1-146 can optionally include receiving a characteristic of the patient fecal sample, and selecting at least one of a plurality of stored donor fecal samples to be provided to the patient using the received characteristic.

In Example 148, any one or more of Examples 1-147 can optionally include receiving a desired characteristic, and selecting at least one of a plurality of stored donor fecal samples to be provided to the patient using the desired characteristic.

In Example 149, the providing the fecal dose to the clinician of any one or more of Examples 1-148 can optionally include providing the fecal dose in a patient-deliverable form, including at least one of an ingestible capsule configured to be delivered to an intestinal tract of the patient through the mouth of the patient, an ampule configured for use in an antegrade gastrointestinal (GI) delivery approach to the intestinal tract of the patient, or an ampule configured for use in a retrograde GI delivery approach to the intestinal tract of the patient.

In Example 150, the providing the kit to the clinician of any one or more of Examples 1-149 can optionally include providing a sterile kit to the clinician.

In Example 151, the providing the kit to the clinician and the providing the fecal dose to the clinician of any one or more of Examples 1-150 can optionally include using expedited shipping.

In Example 152, the expedited shipping of any one or more of Examples 1-151 can optionally include overnight shipping.

In Example 153, any one or more of Examples 1-152 can optionally include screening the patient fecal sample for at least one of a parasite, a pathogen, a disease, or an unhealthy condition of the patient.

In Example 154, any one or more of Examples 1-153 can optionally include providing a kit to the clinician, the kit enabling the clinician to store and transport a patient blood sample from the patient to the central facility, and screening the patient blood sample for at least one of a parasite, a pathogen, a disease, or an unhealthy condition of the patient.

In Example 155, the providing the kit to the clinician of any one or more of Examples 1-154 can optionally include providing a kit enabling the clinician to store and transport a wet fecal sample from the patient to the central facility.

In Example 156, the providing the kit to the clinician of any one or more of Examples 1-155 can optionally include providing a kit enabling the clinician to store, freeze, and transport the wet fecal sample from the patient to the central facility.

In Example 157, a system can include, or can optionally be combined with any portion or combination of any portions of any one or more of Examples 1-156 to include, subject matter that can include means for performing any one or more of the functions of Examples 1-156, or a machine-readable medium including instructions that, when performed by a machine, cause the machine to perform any one or more of the functions of Examples 1-156.

These non-limiting examples described above can be combined in any permutation or combination.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. An oral pharmaceutical composition, comprising:
   a homogenized and filtered donor fecal sample; and
   a cryoprotectant,
   wherein the composition is disposed within an oral tablet or ingestible capsule.

2. The composition of claim 1, wherein the composition is disposed within an oral tablet.

3. The composition of claim 1, wherein the composition is disposed within an ingestible capsule.

4. The composition of claim 1, wherein the oral table or ingestible capsule has an enteric coating.

5. The composition of claim 1, wherein the cryoprotectant comprises a glycol.

6. An oral A pharmaceutical composition, comprising:
   a homogenized and filtered donor fecal sample; and
   a cryoprotectant.

7. The composition of claim 6, wherein the cryoprotectant comprises a glycol.

8. The composition of claim 6, wherein the cryoprotectant comprises glycerol.

9. A pharmaceutical composition, comprising:
   a homogenized and filtered donor fecal sample; and
   a cryoprotectant,
   wherein the composition is provided in a patient-deliverable form.

10. The composition of claim 9, wherein the patient deliverable form comprises a sterile delivery container.

11. The composition of claim 9, wherein the patient deliverable form comprises a bag.

* * * * *

UNITED STATES PATENT AND TRADEMARK OFFICE
CERTIFICATE OF CORRECTION

PATENT NO. : 11,944,654 B2
APPLICATION NO. : 17/886274
DATED : April 2, 2024
INVENTOR(S) : Edwin J. Hlavka It is certified that error appears in the above-identified patent and that said Letters Patent is hereby corrected as shown below:

In the Claims

Claim 6, at Column 22, Line 18, delete "An oral".

Signed and Sealed this
Thirtieth Day of April, 2024

Katherine Kelly Vidal
*Director of the United States Patent and Trademark Office*